US007060671B1

(12) United States Patent
Stott

(10) Patent No.: US 7,060,671 B1
(45) Date of Patent: Jun. 13, 2006

(54) PEPTIDES CONTAINING N-SUBSTITUTED D-AMINO ACIDS FOR PREVENTING β-STRAND ASSOCIATION

(75) Inventor: Kelvin Stott, London (GB)

(73) Assignee: Senexis Limited, Manchester (GB)

( * ) Notice: Subject to any disclaimer, the term of this patent is extended or adjusted under 35 U.S.C. 154(b) by 241 days.

(21) Appl. No.: 10/030,138

(22) PCT Filed: Jul. 28, 2000

(86) PCT No.: PCT/GB00/02923

§ 371 (c)(1),
(2), (4) Date: Apr. 29, 2002

(87) PCT Pub. No.: WO01/07474

PCT Pub. Date: Feb. 1, 2001

(30) Foreign Application Priority Data

Jul. 28, 1999 (GB) ................................. 9917725.5

(51) Int. Cl.
*A61K 38/00* (2006.01)
(52) U.S. Cl. ............................. 514/2; 514/8; 530/350; 530/402; 530/300
(58) Field of Classification Search .................... 514/2, 514/8; 530/300, 350, 402
See application file for complete search history.

(56) References Cited

U.S. PATENT DOCUMENTS 6,610,658 B1 * 8/2003 Findeis et al. ................ 514/17

FOREIGN PATENT DOCUMENTS

| EP | 0885904 A1 | 12/1998 |
|----|------------|---------|
| WO | WO96/28471 | 9/1996 |
| WO | WO97/46547 | 12/1997 |
| WO | WO00/52048 | 9/2000 |

OTHER PUBLICATIONS

Quibell, M. et al. (1995) Improve preparation of beta-amyloid(1-43): structural insight leading to optimised positioning of N-(2-hydroxy-4-methoxybenyl) (Hmb) backbone amide protection, Chem. Soc. Perkin Trans. vol. 1, p. 2019-2024.*

Richardson et al. (2002) Natural beta-sheet proteins use negative design to avoid edge-to-edge aggregation. Proc. Natl. Acad. Sci. U S A. vol. 99, pp. 2754-2759.*
Chalifour et al. (2003) Stereoselective interactions of peptide inhibitors with the beta-amyloid peptide. J. Biol. Chem. vol. 278, pp. 34874-34881.*
Wiesehan et al. (2003) Selection of D-amino-acid peptides that bind to Alzheimer's disease amyloid peptide abeta1-42 by mirror image phage display. Chembiochem. vol. 4, pp. 748-753.*
Janek et al (1999) Water-soluble beta-sheet models which self-assemble into fibrillar structures. Biochemistry. vol. 38, pp. 8246-8252.*
Findeis et al, BIOCHEMISTRY 38, 1999, pp. 6791-6800, Modified-Peptide Inhibitors of Amyloid β-Peptide Polymerization.
Pallitto et al, BIOCHEMISTRY, 38, 1999, pp. 3570-3578, Recognition Sequence Design for Peptidyl Modulators of . . . .
Chitnumsub et al, Bioorganic & Med Chem 7, 1999, pp. 39-59, The Nucleation of Monomeric Parallel β-Sheet-like Structures . . . .
Tjernberg et al, Jour of Biological Chem, vol. 272, No. 19, 1997 pp. 12601-12606, Controlling Amyloid β-Peptide Fibril . . . .
Doig, Chemical Communication, 1997, p. 2153-2154, A three stranded β-sheet peptide in aqueous solution containing . . . .

(Continued)

*Primary Examiner*—Jon Weber
*Assistant Examiner*—Samuel Wei Liu
(74) *Attorney, Agent, or Firm*—Jacobson Holman PLLC

(57) ABSTRACT

Peptide is disclosed which comprises D-enantiomers of amino acids and is capable of interacting with other β-strand structure to form β-sheet, wherein said peptide is selectively Nα-substituted in one edge (first) of the β-strand-forming section of said peptide while the other edge (second) in the opposite orientation to the first edge in view of peptide backbone plane remains Nα-unsubstituted. Such the Nα-substituted peptide is capable of preventing association of said peptide with other β-strand (target) but permits interaction of said peptide with target β-strand in separate peptide-containing molecules through the Nα-unsubstituted edge. The peptide is useful for preventing β-strand association or aggregation.

28 Claims, 5 Drawing Sheets

OTHER PUBLICATIONS

Spillantini et al, Proc Natl Acad Sci, vol. 95, pp. 6469-6473, May 1998, α-Synuclein in filamentous inclusions of Lewy . . . .

Solomon et al, Proc Natl Acad Sci, vol. 93, pp. 452-455, Jan. 1996, Monoclonal antibodies inhibit in vitro fibrillar . . . .

Horwich et al, CELL, vol. 89, pp. 499-510, May 16, 1997, Deadly Conformations—Protein Misfolding in Prion Disease.

Minor, Jr. et al, Ltrs to Nature, vol. 367, pp. 660663, Feb. 17, 1994, Measurement of the β-sheet-forming propensities . . . .

Vives et al, Ltrs in Peptides Sci 4, 1997, pp. 429-436, Structure-activity relationship study of the plasma membrane . . . .

Arima et al, Brain Research 808, 1998, pp. 93-100, Immuno-electron-microscopoic demonstration of NACP/α-synuclein . . . .

Camilleri et al, FEBS Ltrs 341, 1994, pp. 256-258, β-Cyclodextrin interacts with the Alzheimer amyloid β-A4 peptide.

Bronfman et al, Neuroscience Ltrs 218, 1996, pp. 201-203, Laminin inhibits amyloid-β-peptide fibrillation.

Derossi et al, Cell Biology, vol 8, Feb. 1998, pp. 84-87, Trojan peptides: the penetratin system for intracellular . . . .

Hoessli and Robinson, TIG, vol. 14, No. 10, Oct. 1998, pp. 396-402, Protein precipitation: a common etiology in neuro . . . .

Kahn et al, DIABETES, vol. 48, Feb. 1999, pp. 241-253, A Long-Recognized but Underappreciated Pathological Feature of Type . . . .

Lorenzo et al, Proc Natl Acad Sci, vol. 91, pp. 12243-12247, β-Amyloid neurotoxicity requires fibril formation and is . . . .

Vives et al, Jour of Biological Chem, vol. 272, No. 25, 1997, pp. 16010-16017, A Truncated HIV-1 Tat Protein Basic Domain . . . .

Verbeek et al, Biol Chem, vol. 378, Sep. 1997, pp. 937-950, The Role of Amyloid in the Pathogenesis of Alzheimer's Disease.

Sunde et al, Quarterly Rev of Biophysics 31, 1998, pp. 1-39, From the globular to the fibrous state: protein structure . . . .

Williams et al, Biochimica et Biophysica Acta 916, 1987, pp. 200-204, Secondary structure predictions and medium range . . . .

Forloni et al, Progress in Neurobiology, vol. 49, 1996, pp. 287-315, Amyloid in Alzheimer's Disease and Prion-Related . . . .

LeVine III, Protein Science 2, 1993, pp. 404-410, Thioflavine T interaction with synthetic Alzheimer's disease β-amyloid . . . .

Bai et al, PROTEINS 18, 1994, pp. 262-266, Hydrogen Bond Strengh and β-Sheet Propensities: The Role of a Side Chain . . . .

Manavalan et al, BIOPOLYMERS, vol. 19, 1980, pp. 1943-1973, Conformational Energy Studies on N-Methylated Analogs of . . . .

Regan, Current Biology, vol. 4, No. 7, 1994, pp. 656-658, Born to be beta.

Ross, NEURON, vol. 19, Dec. 1997, pp. 1147-1150, Intranuclear Neuronal Inclusions: A Common Pathogenic Mechasism for . . . .

Perutz, TIBS 24, Feb. 1999, pp. 58-63, Glutamine repeats and neurodegenerative diseases: molecular aspects.

Smith et al, SCIENCE, vol. 270, Nov. 10, 1995, pp. 980-982, Guidelines for Protein Design: The Energetics of β Sheet Side . . . .

Alba et al, Protein Science 8, 1999, pp. 854-865, De novo design of a monomeric three-stranded antiparallel β-sheet.

Minor, Jr. et al, NATURE, vol. 371, Sep. 15, 1994, pp. 264-267 Context is a major determinant of β-sheet propensity.

Soto et al, Biochemical and Biophysical Research Comm 226, 1996, pp. 672-680, Inhibition of Alzheimer's amyloidosis by . . . .

Minor, Jr. et al, NATURE, vol. 380, Apr. 25, 1996, pp. 730-734 Context-dependent secondary structure formation of a designed . . . .

Tjernberg et al, Jour of Biological Chem, vol. 271, No. 15, Apr. 12, 1996, Arrest of β-Amyloid Fibril Formation by a . . . .

Ghanta et al, Jour of Biological Chem, vol. 271, No. 47, Nov. 22, 1996, A Strategy for Designing Inhibitors of β-Amyloid . . . .

Derossi et al, Jour of Biological Chem, vol. 271, No. 30, Jul. 26, 1996, Cell Internalization of the Third Helix of the . . . .

Trojanowski et al, Arch Neurol, vol. 55, Feb. 1998, pp. 151-152 Aggregation of Neurofilament and α-Synuclein Proteins in . . . .

Soto et al, Nature Medicine, vol. 4, No. 7, Jul. 1998, pp. 822-826, β-sheet breaker peptides inhibit fibrillogenesis . . . .

Wilmot et al, J. Mol Biology, 203, 1988, pp. 221-232, Analysis and Prediction of the Different Types of β-Turn in Proteins.

Wood et al, Jour of Biological Chem, vol. 271, No. 8, Feb. 23, 1996, pp. 4086-4092, Selective Inhibition of A β Fibril . . . .

Joachim et al, Alzheimer Disease & Assoc Disorders, vol. 6, No. 1, 1992, pp. 7-34, The Seminal Role of β-Amyloid in the . . . .

Babe et al, Protein Science 1, 1992, pp. 1244-1253, Synthetic interface peptides alter dimeric assembly of the HIV 1 and 2 . . . .

Fields et al, Int J Peptide Protein Res 35, 1990, pp. 161-214, Solid phase synthesis utilizing 9-fluorenylmethoxycarbonyl . . . .

Benson et al, Int J Exp Clin Invest 3, 1996, pp. 44-56, Trans-thyretin amyloidosis.

Hanan et al, Int J Exp Clin Invest 3, 1996, pp. 130-133, In-hibitory effect of monoclonal antibodies on Alzheimer's . . . .

Hutchinson et al, Protein Science 7, 1998, pp. 2287-2300, Determinants of strand register in antiparallel β-sheets of . . . .

Miyata et al, J Am Soc Nephrol 9, 1998 pp. 1723-1735, β-2 Microglobulin in Renal Disease.

Zutshi et al, Chemical Biology 2, 1998, pp. 62-66, Inhibiting the assembly of protein-protein interfaces.

Pollack et al, Neuroscience Ltrs 197, 1995, pp. 211-214, Sulfonated dyes attenuate the toxic effects of β-amyloid in . . . .

Price et al, Proc Natl Acad Sci, vol. 90, Jul. 1993, pp. 6381-6384, Alzheimer disease and the prion disorders amyloid . . . .

Schramm et al, Antiviral Research 30, 1996, pp. 155-170, The inhibition of human immunodeficiency virus proteases by . . . .

Merlini et al, Proc Natl Acad Sci, vol. 92, Mar. 1995, pp. 2959-2963, Interaction of the anthracycline . . . .

Hughes et al, Proc Natl Acad Sci, vol. 95, Mar. 1998, pp. 3275-3280, α2-macroglobulin associates with β-amyloid . . . .

Pappolla et al, Jour of Biol Chem, vol. 273, No. 13, Mar. 27, 1998, pp. 7185-7188, Inhibition of Alzheimer . . . .

Koepf et al, Protein Science 8, 1999, pp. 841-853, WW: An isolated three-stranded antiparallel β-sheet domain that . . . .

Derrosi et al, Jour of Biol Chem, vol. 269, No. 14, Apr. 8, 1994, pp. 10444-10450, The Third Helix of the Antennapedia . . . .
Forloni et al, Progress in Neurobiology, vol. 49, 1996, pp. 287-315, Amyloid in Alzheimer's Disease and Prioin-Related . . . .
Selkoe, Annu Rev Cell Biol 10, 1994, pp. 373-403, Cell Biology of the Amyloid β-Protein Precursor and the Mechanism of . . . .
Zutshi et al, J Am Chem Soc 119, 1997, pp. 4841-4845, Targeting the Dimerization Interface of HIV-1 Protease: Inhibition . . . .
Kudva et al, FEBS Ltrs 416, 1997, pp. 117-121, Small heat shock proteins inhibit in vitro Aβ1-42 amyloidogenesis.
Salomon et al, Biochemistry 35, 1996, pp. 13568-13578, Nicotine Inhibits Amyloid Formation by the β-Peptide.
Serpell et al, CMLS Cell Mol Life Sci 53, 1997, pp. 871-887, The molecular basis of amyloidosis.
Smith et al, ACC Chem Res 30, 1997, pp. 153-161, Construction and Design of β-Sheets.
Wisniewski et al, Neurobiology of Disease 4, 1997, pp. 313-328, Biology of Aβ Amyloid in Alzheimer's Disease.
Howlett et al, FEBS Ltrs 417, 1997, pp. 249-251, Hemin and related porphyrins inhibit βamyloid aggregation.
Clark et al, AMHS 104, 1996, pp. 12-18, Islet amyloid in type 2 (non-insulin-dependent) diabetes.
Polymeropoulos, Annals of Neurology, vol. 44 (Suppl 1), Sep. 1998, pp. S63-S64, Autosomal Dominant Parkinson's Disease . . . .
Nesloney et al, Bioorganic & Medicinal Chem, vol. 4, No. 6, 1996 pp. 739-766, Progress Towards Understanding β-Sheet Structure.
Franciskovich et al, Bioorganic & Medicinal Chem, vol. 3, No. 4, 1993, pp. 765-768, A Systematic Evaluation of the Inhibition . . . .
O'Brien et al, Vet Pathol 30, 1993, pp. 317-332, Islet Amyloid Polypeptides: A Review of Its Biology and Potential Roles in . . . .
Mezey et al, Molecular Psychiatry 3, 1998, pp. 493-499, Alpha synuclein is present in Lewy bodies in sporadic Parkinson's . . . .
Baba et al, Amer Jour of Pathology, vol. 152, No. 4, Apr. 1998, pp. 879-884, Aggregation of α-Synuclein in Lewy Bodies of . . . .
Forloni, Neurology 9, 1996, pp. 492-500, Neurotoxicity of β-amyloid and prion peptides.
Lebl et al, Synthetic Peptide Libraries, 1997, pp. 336-392, Methods in Enzymology 289.
Prusiner et al, Amyloid: Int J Exp Clin Invest 2, 1995, pp. 39-65, Prion protein amyloid and neurodegeneration.
Kisilevsky et al, Crit Rev in Biochem and Molec Biol 32 (5), 1997 pp. 361-404, Aβ amyloidogenesis: Unique, or Variation on a . . . .
Trojanowski et al, Cell Death and Differentiation 5, 1998, pp. 832-837, Fatal attractions: abnormal protein aggregation and . . . .
Baandiera et al, Current Medicinal Chem 4, 1997, pp. 159-170, Inhibitors of Aβ Peptide Aggregation as Potential . . . .
Smith et al, Biochemistry 33, 1994, pp. 5510-5517, A Thermo-dynamic Scale for the β-Sheet Forming Tendencies of the Amino . . . .
Pham et al, Nature Structural Biology, vol. 5, No. 2, Feb. 1998 pp. 115-119, A stable single-layer β-sheet without a . . . .

Johnson et al, Tetrahedron Ltrs., vol. 35, No. 3, 1994, pp. 463-466, The N-(2-hydroxybenzyl) Protecting Group for Amide . . . .
Angell et al, Tetrahedron Ltrs, vol. 35, No. 33, 1994, pp. 5981-5984, Comparative Studies of the Coupling of . . . .
Quibell et al, J Chem Soc Perkin Trans 1, 1995, pp. 2019-2024, Improved preparation of β-amyloid(1-43): structural insight . . . .
Quibell et al, J Am Chem Soc 117, 1995, pp. 11656-11668, Synthesis of the 3-Repeat Region of Human Tau-2 by the Solid . . . .
Schramm et al, Biochem and Biophys Res Commun, vol. 194, No. 2, 1993, pp. 595-600, The Inhibition of HIV-1 Protease by . . . .
Schramm et al, Biochem and Biophys Res Commun, vol. 184, No. 2, 1992, Inhibition of HIV-1 Protease by Short Peptides Derived . . . .
Tomiyama et al, Bioc and Biophys Res Commun, vol. 204, No. 1, 1994, Rifampicin Prevents the Aggregation and Neurotoxicity . . . .
Kortemme et al, SCIENCE, vol. 281, Jul. 10, 1998, pp. 253-256, Design of a 20-Amino Acid, Three-Stranded β-Sheet Protein.
Quibell et al, Tetrahedron Ltrs, vol. 35, No. 14, 1994, pp. 2237-2238, Reversible Modification of the Acid Labile 2 . . . .
Miller et al, Drug Development Research 35, 1995, pp. 20-32, Comparison of the Proteolytic Susceptibilities of Homologous . . . .
Hilbich et al, J. Mol. Biol., vol. 228, pp. 460-473, 1992, Substitutions of Hydrophobic Amino Acids Reduce the . . . .
Wood et al, Biochemistry, vol. 34, pp. 724-730, 1995, Prolines and Amyloidogenicity in Fragments of the Alzheimer's Peptide . . . .
Innouye et al, Biophysical Journal, vol. 64, pp. 502-519, Feb. 1993, Structure of β-crystallite assemblies formed by Alzheimer . . . .
Neurobiology of Aging, vol. 11, 1990, Abstracts of Second International Conference on Alzheimer's Disease, p. 302.
Clements et al, Neuroscience Ltrs., vol. 161, 1993, pp. 17-20, Effects of the mutation GLU$^{22}$ to Gln and Ala$^{21}$ to Gly on the . . . .
Jayawickrama et al, Journal of Biomolecular . . . , vol. 13, No. 2, 1995, pp. 229-244, Conformational Analysis of the . . . .
Brack et al, Origins of Life & Evolution . . . , vol. 20, 1990, pp. 139-144, Chemical Activity of Simple Basic Peptides.
Wen et al, Journal of Biol Chem, vol. 268, No. 22, Aug. 5, 1993, pp. 16401-16405, Structure-Function Relationships in an . . . .
Kirschner et al, Proc Natl Acad Sci, vol. 84, Oct. 1987, pp. 6953-6957, Synthetic peptide homologous to β protein from . . . .
Orlando et al, Biochem & Biophys Research Comm, vol. 184, No. 2, Apr. 30, 1992, Covalent Modification of Alzheimer's Amyloid . . . .
Schwarzman et al, Proc Natl Acad Sci, vol. 91, Aug. 1994, pp. 8368-8372, Transthyretin sequesters amyloid β protein and prevents . . . .
Guichard et al, Proc Natl Acad Sci, vol. 91, Oct. 1994, pp. 9765-9769, Antigenic mimicry ofnational L-peptides with retro- . . . .
Evans et al, Proc Natl Acad Sci, vol. 92, Jan. 1995, pp. 763-767, Apoliprotein E is a kinetic but not a thermodynamic inhibitor . . . .

* cited by examiner

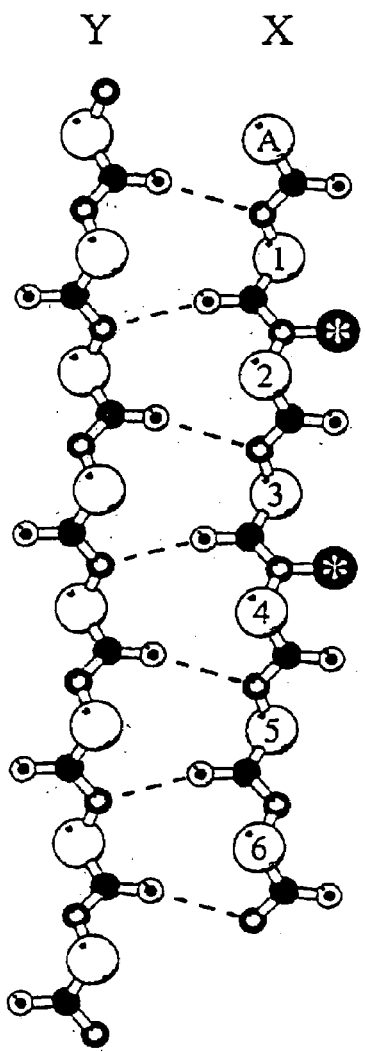
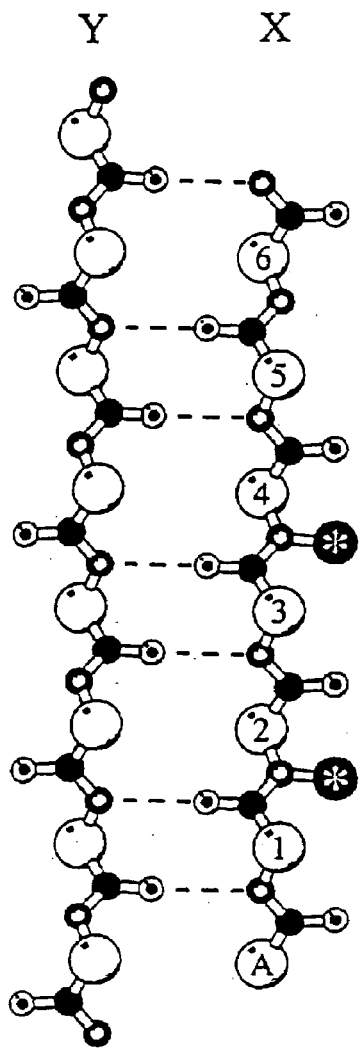
ATOM KEY
◯ Cα　● C　◉ N　⊙ O　✱ C (Nα-methyl)

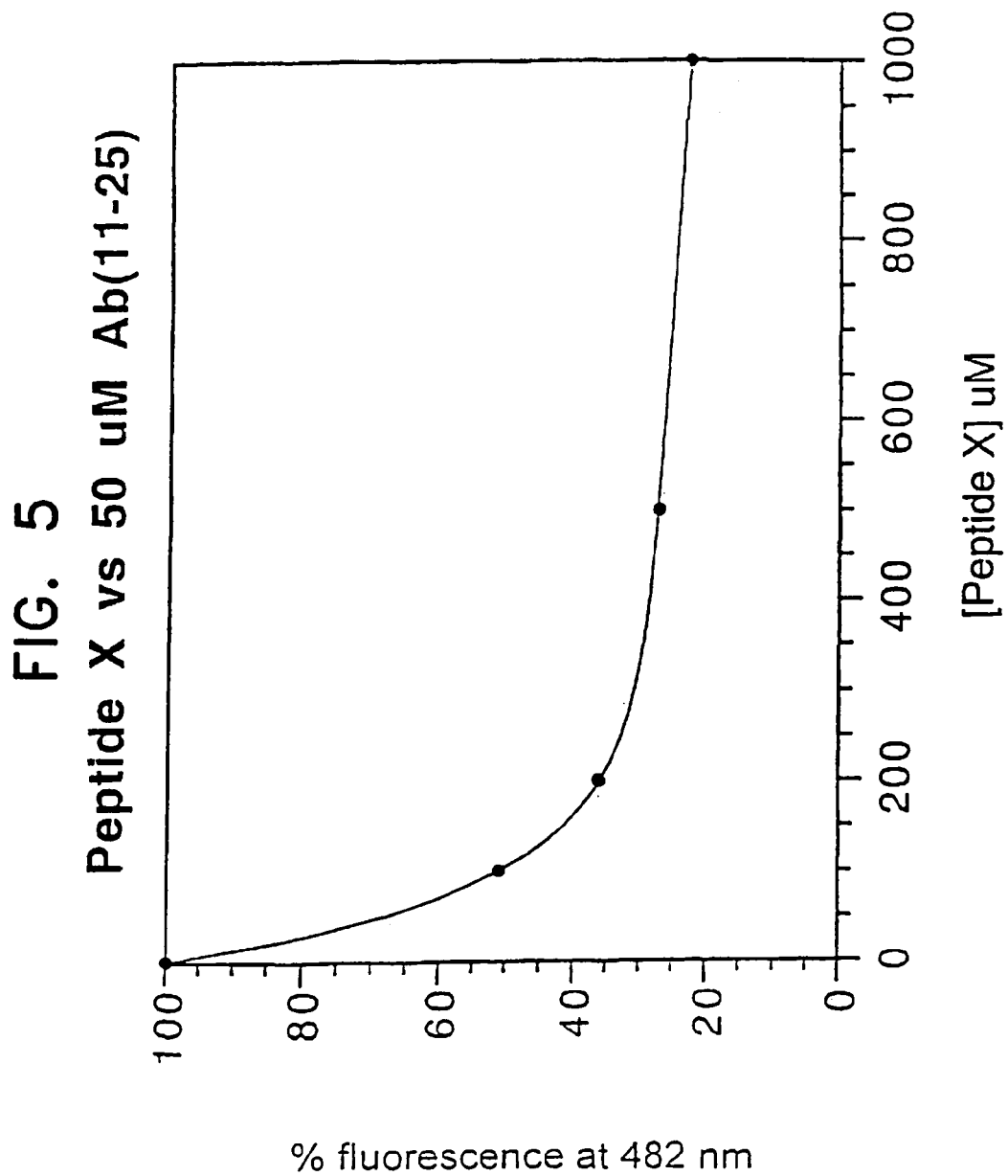

US 7,060,671 B1

PEPTIDES CONTAINING N-SUBSTITUTED D-AMINO ACIDS FOR PREVENTING β-STRAND ASSOCIATION

This is a nationalization of PCT/GB00/02923, filed Jul. 28, 2000 and published in English.

The present invention relates to a class of peptide-based compounds that bind specifically to target β-strands and thereby inhibit their association into β-sheets and insoluble β-fibres. In particular, the invention relates to peptides composed of D-enantiomers of amino acids at least some of which are modified by Nα substitution.

A large number of terribly distressing, currently incurable neurodegenerative diseases are caused by the aggregation of proteins or peptides into insoluble cytotoxic inclusions or amyloid-like plaques within the brain: Alzheimer's disease (AD), which is the most common form of senile dementia and the fourth most common cause of death in the developed world, is caused by the aggregation of a 39–43-residue Aβ peptide fragment of a larger amyloid precursor protein (Forloni, 1996; Forloni et al., 1996; Joachim and Selkoe, 1992; Price et al., 1993; Selkoe, 1994; Verbeek et al., 1997; Wisniewski et al., 1997); Parkinson's disease (PD) and at least one form of dementia (Dementia with Lewy Bodies, or DLB) are caused by the aggregation and incorporation of α-synuclein into intracytoplasmic inclusions called Lewy bodies (Arima et al., 1998; Baba et al., 1998; Mezey et al., 1998; Polymeropoulos, 1998; Spillantini et al., 1998; Trojanowski et al., 1998; Trojanowski and Lee, 1998); prion-related encephalopathies such as bovine spongiform encephalopathy (BSE, or 'mad cow disease') and its human forms Creutzfeldt-Jakob disease (CJD) and kuru are caused by the self-catalysed misfolding and aggregation of meta-stable proteins known as prions (Forloni, 1996; Forloni et al., 1996; Horwich and Weissman, 1997; Price et al., 1993; Prusiner and Dearmond, 1995); several dominantly inherited neurodegenerative diseases including Huntington's disease (HD), X-linked spinal and bulbar muscular atrophy (SBMA), dentatorubral-pallidoluysian atrophy (DRPLA), and at least five genetically distinct forms of spinocerebellar ataxia (SCA types 1, 2, 3, 6 and 7; SCA3 is better known as Machado-Joseph disease, or MJD) are caused by the aggregation and incorporation of proteins or protein fragments containing abnormally expanded glutamine repeats into intranuclear inclusions (Perutz, 1999; Ross, 1997).

In addition to these and undoubtedly many other, as yet unidentified neurodegenerative diseases, several non-neurodegenerative but equally distressing diseases are caused by the aggregation of proteins or peptides in other parts of the body. For example: type II diabetes mellitus is caused by aggregation of the 37-residue islet amyloid polypeptide (IAPP or amylin) within the islets of Langerhans in the pancreas (Clark et al., 1996; Kahn et al., 1999; Obrien et al., 1993); familial amyloid polyneuropathy and senile systemic amyloidosis are caused by the aggregation of full-length transthyretin and fragments thereof (Benson and Uemichi, 1996); and dialysis-related amyloidosis is caused by the aggregation of $β_2$-microglobulin (Miyata et al., 1998).

In all these diseases, which are collectively known as amyloidoses, the proteins or peptides involved aggregate into insoluble β-fibres by the intermolecular association of β-strands into extended β-sheets; these β-fibres are deposited in inclusions or amyloid-like plaques which bring about progressive cell death by some unknown mechanism. For more general reviews on the amyloidoses and their mechanisms, see references (Kakizuka, 1998; Kisilevsky and Fraser, 1997; Serpell et al., 1997; Sunde and Blake, 1998; Wisniewski et al., 1998).

Although it remains to be determined how the aggregation of peptides and proteins into insoluble inclusions results in the progressive death of cells, it is clear that the most effective general way to treat the diseases would be to prevent the formation of these cytotoxic inclusions using some agent that specifically inhibits the aggregation of proteins and peptides into insoluble β-fibres. For one reason or another, however, none of the existing inhibitors of protein and peptide aggregation are suitable for use as therapeutic agents:

1) Simple organic compounds that act as protein denaturants such as guanidinium chloride, urea, detergents, and many organic solvents are very effective inhibitors of protein and peptide aggregation. However, they tend to destabilise correctly folded proteins and disrupt sensitive protein—protein interactions within the cell at working concentrations because they are too simple in form to inhibit protein and peptide aggregation specifically. As a consequence they are toxic to cells, and are therefore unsuitable for use as therapeutic agents.

2) A number of more complex organic compounds have been found to inhibit protein and peptide aggregation somewhat more specifically. They include: β-cyclodextrin (Camilleri et al., 1994), congo red and other sulphonated dyes (Burgevin et al., 1994; Lorenzo and Yankner, 1994; Pollack et al., 1995), nicotine (Salomon et al., 1996), hemin and related porphyrins (Howlett et al., 1997), anthracycline 4'-iodo-4'-deoxydoxorubicin (Merlini et al., 1995), hexadecyl-N-methylpiperidinium bromide (Wood et al., 1996), melatonin (Pappolla et al., 1998), and rifampicin (Tomiyama et al., 1994). None of these compounds have been found to be suitable for use as therapeutic agents, however, therefore they are best regarded as structural hits in the search for more active and pharmacologically useful compounds. For a review on these compounds as inhibitors of Aβ peptide aggregation, see reference (Bandiera et al., 1997).

3) Large proteins such as chaperonins or heat shock proteins (Kudva et al., 1997), α2-macroglobulin (Hughes et al., 1998), laminin (Bronfman et al., 1996), and monoclonal antibodies (Hanan and Solomon, 1996; Solomon et al., 1996) can be extremely effective and specific as inhibitors of protein and peptide aggregation because of their size and complexity. However, they are too large to penetrate cell membranes and the blood-brain barrier, they are susceptible to aggregation and proteolysis, and they tend to be immunogenic.

4) Simple peptides can also inhibit protein and peptide aggregation effectively and specifically, and they are at least small enough to penetrate cell membranes and the blood-brain barrier, which also makes them less likely to be immunogenic than large proteins. However, there is currently a conflict between the solubility, hydrophobicity, and potency of these peptides, as well as a problem of proteolytic degradation:

In Alzheimer's disease, for example, the 39–43-residue Aβ peptide aggregates into amyloid fibrils by the intermolecular association of five-residue peptide segments comprising the sequence KLVFF (SEQ ID NO: 1) (corresponding to residues 16–20 of the Aβ peptide) (Tjernberg et al., 1997; Tjernberg et al., 1996). The peptide segments form β-strands which associate to form an extended antiparallel β-sheet by means of hydrophobic interactions between their side chains and hydrogen bonds between their backbone amide groups. This fibrogenic association can be inhibited by short peptides which also contain the KLVFF sequence (SEQ ID NO: 1) or a homologous sequence, such as Ac-QKLVFF-NH$_2$ (Tjernberg et al., 1996), GQKLVFFAED-VGG-[NH(CH$_2$)$_5$CO]-K$_6$ (Ghanta et al., 1996), and KKLVFFA (SEQ ID NO: 4) (Tjernberg et al., 1997). These peptides form β-strands which compete for association with the homologous sequence in the Aβ peptide and thereby hinder its aggregation. The first of these peptides has a limited solubility in aqueous solutions because it too can aggregate into extended β-sheets. The latter two peptides, on the other hand, are more water-soluble because they contain more polar groups, but are consequently too hydrophilic to penetrate cell membranes and the blood-brain barrier. Peptides can be made more soluble without compromising their hydrophobicity by including proline residues rather than polar residues. For example, the peptides RDLPFFPVPID, LPFFPVD, and LPFFD have a similar degree of hydrophobicity as the Aβ peptide, but are highly soluble in aqueous solutions because the proline residues sterically prevent them from forming β-strands which aggregate into extended β-sheets (Soto et al., 1996; Soto et al., 1998). However, these peptides are less potent inhibitors of Aβ-peptide aggregation because the β-strand conformation is actually required for making strong and specific interactions with the β-strands formed by the Aβ peptide, in order to inhibit their aggregation. In short, nobody has discovered how to prevent the peptides from aggregating in aqueous buffers without compromising their hydrophobicity, which is required for effective penetration of cell membranes and the blood-brain barrier, or their potency as inhibitors of protein and peptide aggregation.

In addition to this problem of solubility versus hydrophobicity and potency, all the peptides mentioned above are extremely susceptible to degradation by proteolytic enzymes because they consist entirely of Nα-unsubstituted α-L-amino acid residues, and are therefore unsuitable for use as therapeutic agents. This particular problem has been addressed by designing peptides that consist only of α-D-amino acid residues, which are not recognised by proteolytic enzymes (Miller et al., 1995). For example, all-D-[RDLPFF-PVPID] (Soto et al., 1996) and all-D-[LFLRR] (Tjernberg et al., 1997) are highly resistant to enzyme-catalysed proteolysis as expected, but these peptides still face the problem of conflict between solubility in aqueous buffers, ability to penetrate cell membranes and the blood-brain barrier, and ability to inhibit the aggregation of other proteins and peptides into insoluble β-fibres.

It is known that peptides containing Nα-substituted or α-D-amino acid residues are much less susceptible to enzyme-catalysed proteolysis than peptides which consist only of Nα-unsubstituted α-L-amino acid residues because neither Nα-substituted nor α-D-amino acid residues are not recognised by proteolytic enzymes (Miller et al., 1995). Peptides containing Nα-substituted amino acid residues are also much less likely to aggregate into insoluble β-fibres in aqueous solutions because the Nα atoms of these residues are not available for hydrogen bonding and, moreover, because their Nα substituents sterically disallow the association of β-strands. A peptide has been designed containing Nα-methyl amino acid residues which folds into a three-stranded β-sheet, but which does not aggregate into extended β-sheets because the Nα-methyl groups of these residues sterically prevent it from doing so (Doig, 1997). In this peptide, the two peripheral β-strands each contain a sequence of two Nα-methyl alanine residues separated by a single Nα-unsubstituted alanine residue, so that all four Nα-methyl groups lie along the outer edges of these two β-strands, while the inner edges remain free to associate with the central β-strand, thereby forming the three-stranded β-sheet. However, it has not previously been reported that such a peptide is, in isolation, able to associate with β-strands formed by other protein or peptide molecules and thereby inhibit their aggregation into extended β-sheets and insoluble β-fibres. Moreover, it has not previously been reported that a peptide comprising Nα-substituted and Nα-unsubstituted α-D-amino acid residues is able to associate specifically with β-strands formed by other protein or peptide molecules and thereby inhibit their aggregation into extended β-sheets and insoluble β-fibres.

SUMMARY OF THE INVENTION

In accordance with a first aspect of the present invention, therefore, there is provided a chemical compound or composition comprising a peptide, which peptide comprises a β-strand-forming section of peptide which forms a β-strand and associates as such with a target β-strand formed by a separate peptide-containing molecule, or comprising a component which mimics the structure and action of said β-strand-forming section of peptide, wherein the β-strand-forming section of peptide comprises a sequence of at least four consecutive α-D-amino acid residues, all of which sterically permit the β-strand-forming section of peptide to form a β-strand, and at least one of which is an Nα-substituted α-D-amino acid residue, and any two successive Nα-substituted α-D-amino acid residues are separated by an odd number of consecutive Nα-unsubstituted α-D-amino acid residues.

A β-strand is a section of peptide whose backbone takes on the form of an extended ribbon; the side chains of consecutive residues in a β-strand protrude from alternate sides of the plane of the ribbon, while the NH and CO components of the backbone peptide groups lie along the two edges of the ribbon. β-strands are regular structures that are only formed by sections of peptide which consist solely of a L amino α-L-amino acid residues or solely of α-D-amino acid residues; the phi and psi angles of each amino-acid residue in a β-strand are close to −120° and +120° respectively. β-strands are not stable in isolation, and exist only when two or more of them are associated to form a parallel or antiparallel β-sheet. The individual β-strands in a β-sheet are held together side by side and edge to edge in either parallel or antiparallel orientation by hydrogen bonds between the NH and CO components of their backbone peptide groups, as well as by additional non-covalent interactions between their side chains. A β-strand has two edges, each of which can support the association of another β-strand in this way. A β-sheet can therefore be extended indefinitely by the progressive addition of more β-strands to the free edges of its two peripheral β-strands; this eventually results in the formation of insoluble β-fibres.

The mechanism by which β-strands formed by proteins and peptides aggregate into β-sheets and thereby insoluble β-fibres is illustrated schematically in FIG. 1. The peptides according to the invention inhibit the aggregation of proteins and peptides into insoluble β-fibres by binding specifically to the free edges of β-strands, thereby sterically hindering their association into extended β-sheets. The entire peptide may be involved in the formation of a β-strand, or only a section thereof, as referred to above. Where only a section of the peptide is involved in β-strand formation, it may be referred to as the "β-strand-forming section".

A "section", as referred to herein, is any part of an entity such as a peptide. Thus, when applied to peptides, "section" refers to a sequence of contiguous amino-acid residues within, or at one end of, the peptide. The length of a "section" of peptide will depend upon the desired application to which the section is to be put; for example, β-strand-forming section of peptide may be at least four amino-acids in length, preferably longer, as set out below. The section may encompass the whole of the peptide, or any part thereof. For example, it may encompass 10%, 25%, 50%; 75%, 90% or 100% of the peptide.

"Successive", as used herein, refers to any two defined amino-acid residues which follow one another in a sequence, whether or not they are contiguous in sequence. Thus, two successive Nα-substituted amino-acid residues may be separated, if they are separated, by one or more Nα-unsubstituted amino-acid residues.

"Consecutive", as used herein, refers to any two defined amino-acid residues which follow one another in contiguous sequence. Thus, two consecutive Nα-unsubstituted amino-acid residues are adjacent in an amino-acid sequence.

According to the present invention, the chemical compound or composition is separate from the target. The target is thus a discrete molecule, which either is a peptide or comprises a peptide. The target molecule may thus be a peptide, a protein comprising a β-sheet peptide or section of peptide, a derivative of a protein, or any other molecule which is capable of forming at least one β-strand.

The invention moreover relates to chemical compounds and compositions comprising components which mimic the structure and action of a β-strand and are thus peptide mimics. A "peptide mimic" refers to a peptide wherein one or more of the backbone peptide groups or side-chain groups have been replaced by another chemical group of similar stereochemistry and ability to form favourable non-covalent interactions with the target β-strand. For example, each backbone peptide group (CONH) could be replaced by one of the following groups: CSNH (thioamide); COO (ester); CSO/(thioester); CSS (dithioester); $COCH_2$ (ketone); $CSCH_2$ (thioketone); $SO_2NH$ (sulphonamide); $SOCH_2$ (sulphoxide); $SO_2CH_2$ (sulphone); $SO_2O$ (sulphonate). Each N-substituted backbone peptide group could be replaced by an N- or C-substituted form of one of the following groups: CSNH (thioamide); $COCH_2$ (ketone); $CSCH_2$ (thioketone); $SO_2NH$ (sulphonamide); $SOCH_2$ (sulphoxide); $SO_2CH_2$ (sulphone). And each side chain could be replaced by another group having a similar stereochemistry or arrangement of polar and non-polar atoms, as long as any particular features which are essential for association with the target β-strand are preserved.

The use of Nα-substituted α-D-amino acid is highly advantageous. All α-D-amino acid are resistant to protease attack, and Nα-substituted α-D-amino acid are also suitable for sterically hindering β-sheet formation. Resistance to protease attack is a preferred property in the context of the present invention.

In a second aspect of the present invention, there is provided a method for inhibiting or reversing the association of a target β-strand into a β-sheet or β-fibre, comprising exposing the target β-strand to a chemical compound or composition according to the first aspect of the invention and allowing or inducing the chemical compound or composition to associate with the target β-strand.

Optionally, in the method according to the preceding aspect of the invention, other agents capable of destabilising β-sheet formation may be used together with the peptides of the invention. For example, in vitro use of a peptide according to the invention and a chaotrope, such as Guanidiniun hydrochloride, is effective in preventing aggregation of β-strands to from β-sheets in solution.

In a third aspect, there is provided a method for inhibiting or reversing the aggregation of proteins or peptides, comprising contacting the proteins or peptides with a chemical compound or composition according to the first aspect of the invention.

In a fourth aspect, the invention provides a method for assisting in the refolding of denatured or aggregated proteins or peptides, comprising contacting the aggregated proteins or peptides with a chemical compound or composition according to the first aspect of the invention.

In a fifth aspect, there is provided a chemical compound or composition according to the first aspect of the invention for use in medicine.

In a sixth aspect, there is provided the use of a chemical compound or composition according to the first aspect of the invention for the preparation of a composition for the diagnosis, study, or treatment of a disease caused by the aggregation of proteins or peptides into insoluble β-fibres.

In a seventh aspect, the invention provides a method for inhibiting the oligomerisation or association of protein subunits, comprising exposing the protein subunits to a chemical compound or composition according to the first aspect of the invention.

The method of the seventh aspect may be applied, for example, to the inhibition of an enzyme whose catalytic activity depends on its oligomerisation by the association of β-strands, either in vitro or in vivo.

In an eighth aspect, there is provided a method for indicating the presence or location of β-strands, β-sheets, or β-fibres, comprising exposing a test sample to a chemical compound or composition according to the first aspect of the invention which comprises a detectable moiety, removing any unbound chemical compound or composition, and assessing the test sample for the presence of the detectable moiety.

The test sample may be a histological sample and the chemical compound or composition may be used as a histochemical stain or indicator.

In a ninth aspect, the invention relates to a method for affinity or protein-renaturation chromatography, comprising the steps of covalently attaching a chemical compound or composition according to the first aspect of the invention to a solid matrix, resin, or support; passing a test sample over the column; and separating the desired treated product from the column.

In a tenth aspect, the invention provides a combinatorial library comprising chemical compounds or compositions according to the first aspect of the invention.

BRIEF DESCRIPTION OF THE FIGURES

in FIG. 1 this interaction is represented by the mutual insertion of circular tabs into the circular holes of associated jigsaw pieces, which may lead to the production of extended chains of jigsaw pieces representing the extended β-sheets and insoluble β-fibres.

FIGS. 3 and 4 show how Peptide X SEQ ID NO: 2) forms a β-strand (X) and associates as such with one edge of a target β-strand (Y) formed by a segment of the Aβ peptide or some other peptide-based molecule in either orientation to form a parallel (FIG. 3) or antiparallel (FIG. 4) two-stranded β-sheet complex, thereby sterically hindering the association of other β-strands with that edge of the target β-strand. In each of these two figures: the target β-strand comprises a sequence of eight consecutive α-L-amino acid residues, the Cα atoms of which have not been labelled; the Cα atoms of the six α-D-amino acid residues of Peptide X SEQ ID NO: 2) are numbered from the N-terminus, while the Cα atom of its N-terminal acetyl group is indicated by a letter A; only the non-hydrogen backbone atoms of these two β-strands—including the Nα-methyl carbon atoms of the two Nα-methyl-α-D-amino acid residues (residues 2 and 4) of Peptide X SEQ ID NO: 2)—are shown, and are represented by symbols defined by the atom key below the figures; hydrogen bonds between backbone amide groups of the two β-strands are indicated by dashed lines.

FIG. 5 is a graph showing the prevention of Alzheimer's Aβ peptide aggregation into β-sheet structures after administration of Peptide X SEQ ID NO: 2). A 50% reduction in Alzheimer's Aβ peptide aggregation is seen at a Peptide X SEQ ID NO: 2) concentration of 100 mM.

DETAILED DESCRIPTION OF THE INVENTION

Figure 1:
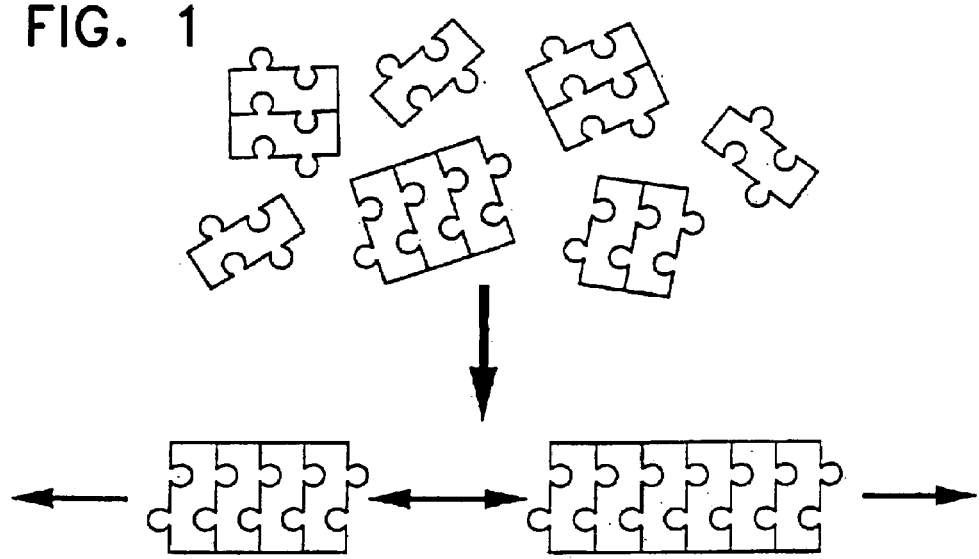
FIG. 1 illustrates schematically how β-strands associate into extended β-sheets and thereby insoluble β-fibres. In this figure, the β-strands are represented by white jigsaw pieces which have both a circular tab and a circular hole of the same size on each of their two long edges, representing the CO and NH components of the backbone amide groups along the two edges of the β-strands. The β-strands may associate in either the parallel or antiparallel orientation into extended β-sheets and insoluble β-fibres by the formation of hydrogen bonds between these CO and NH components.
Figure 2:
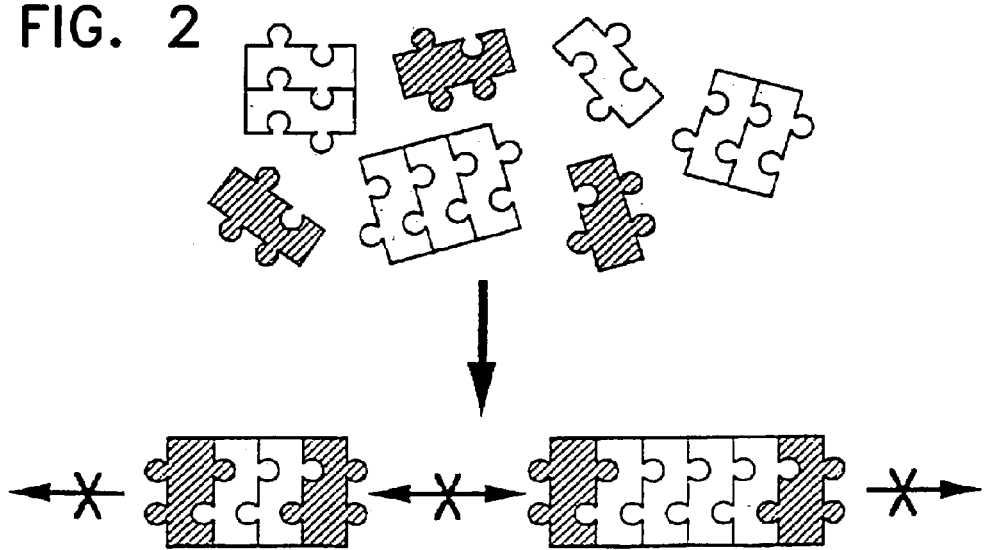
FIG. 2 illustrates schematically how β-strands formed by the β-strand-forming sections of peptide in the peptides of the invention are able to inhibit the aggregation of target β-strands formed by other proteins and peptide molecules into extended β-strands and insoluble β-fibres. In this figure, the target β-strands are represented by white jigsaw pieces which have both a circular tab and a circular hole of the same size on each of their two long edges, just as they are in FIG. 1, while the β-strands formed by the β-strand-forming sections of peptide are represented by shaded jigsaw pieces. One edge of these shaded jigsaw pieces has both a circular tab and a circular hole, representing the CO and NH components of the backbone amide groups which lie along the free edge of the β-strand formed by the β-strand-forming is section of peptide. This edge of the shaded jigsaw pieces is identical to both edges of the white jigsaw pieces, and can therefore be joined to the white jigsaw pieces in either parallel or antiparallel orientation just as the white jigsaw pieces are able to be joined to each other. The other edge of the shaded jigsaw pieces, however, has two circular tabs but no circular hole, representing the fact that one, some, or all of the backbone NH groups along one edge of the β-strand formed by the β-strand-forming section of peptide are sterically blocked by the Nα-substituents which lie along it. This edge of the shaded jigsaw pieces is consequently unable to be joined to any other jigsaw piece, whether it be white or shaded. Therefore, when the single-tab edge of a shaded jigsaw piece is joined in either the parallel or antiparallel orientation to either single-tab edge of a white jigsaw piece, which may or may not form part of a longer chain of such pieces, no other jigsaw piece may subsequently be joined to that edge of the white jigsaw piece, and elongation of a chain is thereby blocked as shown, unless the terminal shaded jigsaw piece is first removed. In just the same way, the β-strands formed by the β-strand-forming section of peptide bind to the target β-strands formed by other protein and peptide molecules and thereby inhibit their aggregation into extended β-strands and insoluble β-fibres. This jigsaw model thus clearly illustrates the fundamental concept of the present invention.

The peptides according to the invention inhibit the aggregation of proteins and peptides into insoluble β-fibres by binding specifically to the free edges of β-strands, thereby sterically hindering their association into extended β-sheets. They do this substantially as follows:

The peptide according to the present invention comprises a section which is able to form a β-strand, because it consists solely of α-D-amino acid residues which sterically permit it to do so. On top of this, the steric constraints imposed by the Nα-substituted α-D-amino acid residue(s) and by any β-branched α-D-amino acid residue(s) in the β-strand-forming section of peptide may serve to encourage β-strand formation. When the β-strand-forming section of peptide forms a β-strand, the Nα-substituents of its Nα-substituted α-D-amino acid residues are positioned, by design, so as to lie along only one of its two edges. The Nα-substituted residues are spaced such that they are separated by odd numbers of residues, since the repeating unit of a β-strand is two residues. For example, between any two successive Nα-substituted residues there may lie 1 or 3 Nα-unsubstituted residues.

The Nα-substituted edge of the β-strand is unable to associate with other β-strands formed by the β-strand forming section of peptide because the Nα-substituents which lie along it sterically prevent it from doing so. The other, free edge of this β-strand is able to do so, and may associate in either the parallel or antiparallel orientation with a free edge of a target β-strand formed by another protein or peptide molecule by means of hydrogen bonds between their backbone peptide groups and additional non-covalent interactions between their side chains. This target β-strand is most likely to be one of the two peripheral β-strands of an existing β-sheet, but could also be a single, isolated β-strand that forms only as it associates with the β-strand formed by the β-strand-forming section of peptide. Either way, the result of this association is the formation of a β-sheet complex wherein the β-strand formed by the β-strand-forming section of peptide sterically blocks the association of other β-strands with the now associated edge of the target β-strand, thereby preventing the formation of an extended β-sheet and the deposition of insoluble β-fibres. For example, if the target β-strand is one of the two peripheral β-strands of an existing β-sheet, then the association of the β-strand formed by the β-strand-forming section of peptide with the free edge of that target β-strand sterically blocks the association of other β-strands with that edge of the target β-strand, thereby preventing extension of the β-sheet in that direction. Extension of the β-sheet in the other direction may be prevented in the same way by association of the β-strand formed by the β-strand-forming section of peptide with the free edge of the other peripheral β-strand of the β-sheet. Isolated target β-strands may be prevented from associating with each other by simultaneous association of both edges with two β-strands formed by the β-strand-forming section of peptide. In this case, the resulting three-stranded β-sheets can not be extended in either direction due to steric hindrance by the Nα substituents which lie along the outer edges of both the peripheral β-strands.

As used herein, a "peptide" is a polymer in which the monomers are amino acids and are joined together by peptide bonds. The length of a β-strand-forming section of peptide according to the invention will be determined empirically, as described in detail below; however, the β-strand-forming section of peptide is at least 4 amino acid residues in length, and preferably between about 4 and about 50 amino acid residues in length; advantageously between about 4 and about 16 amino acid residues in length, and most preferably between about 5 and about 10 amino acid residues. Preferably, the β-strand-forming section of peptide is no longer than the target β-strand, and at least as long as the aggregation-causing section of the target β-strand.

The amino-acid monomers of which the β-strand-forming section of peptide is constructed are α-D-amino acids, meaning that they are of the D-enantiomeric from as opposed to the L-enantiomeric form. D-amino acids, which commonly occur in nature, are susceptible to digestion by protease enzymes if unprotected. Nα-substituted α-D-amino acids are α-D-α-D-amino acids which carry a substituent, which is not hydrogen, on the α-N atom, whilst Nα-unsubstituted α-D-amino acids have no substituent at this position. Preferred substituents useful for practising the subject invention are set forth below. In general, however, the substituents must be large enough to sterically hinder the association of β-strands, and preferably large enough to hinder or prevent proteolytic degradation of the peptide but they must not hinder the β-strand forming section of peptide from forming a β-strand.

As used herein, "destabilising", when applied to β-sheets and β-sheet formation, refers to the inhibition of β-strand aggregation into β-sheet structures and preferably the prevention of β-strand aggregation. Advantageously, it refers to the reversal of β-strand aggregation and actual disruption of β-sheet structures. Reversal may be complete or partial; in general, reversal indicates that p-sheet structures revert to unassociated β-strands, or are split up into smaller β-sheets. "Hinder", "inhibit" and "prevent", as used above, refer to a reduction in β-strand aggregation ranging from partial to substantially complete. For example, β-strand aggregation may be reduced by 20%, 30%, 50%, 75% or more, preferably about 90% or 100%.

The side chains used in β-strand-forming sections of peptide according to the invention moreover allow or favour the formation of β-strands. "Allow", as used herein, means that the formation of β-strands is not impeded. "Favour" means that such formation is facilitated with respect to any selected amino-acid which merely allows β-strand formation.

The concept of favouring or allowing β-strand formation may be expressed in terms of β-sheet propensity values for amino-acid residues. β-sheet propensity is a measure of the incidence of particular amino-acids in β-sheets formed by natural proteins; it has been found that the propensity value correlates very well with the thermodynamic considerations which govern β-sheet formation by amino-acid residues. See, for example, Williams et al., (1987); Wilmot and Thornton, (1988); Kim and Berg, (1993); Smith et al., (1994); Minor and Kim, (1994a); Regan, (1994); and Bai and Englander, (1994). Advantageously, residues incorporated into the β-strand-forming section of peptide have a β-sheet propensity of at least about 1.00.

Design of Peptides According to the Invention

In order that the β-strand-forming section of peptide is able to form a β-strand, it must consist solely of α-D-amino acid residues which sterically permit the β-strand-forming section of peptide to form a β-strand. Proline, for example, cannot be included in the β-strand-forming section of peptide except at its very ends because its side chain is joined back onto its backbone nitrogen atom, and therefore it is unable to adopt the phi angle required to form a β-strand.

In order that the β-strand formed by the β-strand-forming section of peptide associates strongly enough with a target β-strand to inhibit its aggregation into insoluble β-fibres, it must be at least four amino-acid residues in length. A β-strand consisting of three or fewer amino-acid residues would not interact with a target β-strand strongly enough to hinder the association of other β-strands with that target β-strand. In general, the β-strand-forming section of peptide may be any length greater than three residues (i.e. four or more), but in practice should be no longer than the target β-strand, and should preferably be at least as long as the segment of that target β-strand which is directly responsible for its aggregation.

This is because the aggregation-causing segment of the target β-strand is likely to comprise a sequence of residues having hydrophobic or amide-containing side chains, which can form the strongest interactions with the adjacent side chains of an associated β-strand in aqueous solutions. It is this aggregation-causing segment of the target β-strand with which the β-strand-forming section of peptide is preferably designed to associate. Whilst the β-strand-forming section of peptide according to the invention may be shorter, the same length or longer than the aggregation-causing segment of the target β-strand, there is no need for the β-strand forming section of peptide to be any longer than the target β-strand itself, because any additional residues in the β-strand-forming section of peptide are unlikely to interact strongly with the residues which flank the target β-strand, if such residues are not in a β-strand structure.

The target β-strand, the aggregation-causing segment of that target β-strand and therefore the optimal length for the β-strand-forming section of a peptide according to the present invention, may be determined empirically. For example, the target β-strand may be identified as a section of peptide in a protein or peptide molecule which forms a β-strand and undesirably aggregates or associates as such with other β-strands to form a β-sheet or β-fibre. The aggregation-causing segment of this target β-strand can then be identified as a section of at least four residues mostly having hydrophobic and/or amide-containing side chains, or can be determined experimentally by investigating the association properties of short segments of the target β-strand or of single-residue mutants of the target β-strand. For example, a section of the 39–43-residue Alzheimer's Aβ peptide forms a β-strand and undesirably aggregates as such into insoluble β-fibres. This β-strand is therefore identified as the target β-strand, and its aggregation-causing segment has been identified as having the sequence KLVFF SEQ ID NO: 1) by investigating the association properties of short segments of the Aβ peptide and single-residue mutants thereof: truncation of this segment at either end, or substitution of any of its residues by alanine dramatically reduced the tendency of the Aβ peptide to aggregate into insoluble β-fibres (Tjernberg et al., 1997; Tjernberg et al., 1996).

It will be appreciated by those skilled in the art that similar procedures may be used to identify target β-strands in proteins other than Aβ, or to identify alternative target β-strands in Aβ, using similar (or other) procedures, as known in the art and/or described herein.

The β-strand-forming section of peptide according to the invention is preferably designed to form a β-strand and associate as such in the parallel orientation with this aggregation-causing segment of the target β-strand to form a parallel β-sheet complex. Preferably, it is designed as follows.

The β-strand-forming section of peptide preferably contains the same number of residues as the aggregation-causing segment of the target β-strand, and advantageously comprises a sequence of alternating Nα-methyl-α-D-amino acids and Nα-unsubstituted α-D-amino acid residues. The side chains of the residues in the β-strand-forming section of peptide are complementary to those of the aggregation-causing segment of the target β-strand in the same order, by which is meant the side chain of the first residue of the β-strand-forming section of peptide is chosen to form a favourable non-covalent interaction with the side chain of the first residue of the aggregation-causing segment of the target β-strand, and so on. For example: if the first residue of the aggregation-causing segment of the target β-strand has an amide-containing side chain, then the first residue of the β-strand-forming section of peptide should also have an amide-containing side chain; if the first residue of the aggregation-causing segment of the target β-strand has a hydrophobic side chain, then the first residue of the β-strand-forming section of peptide should also have a hydrophobic side chain; if the first residue of the aggregation-causing segment of the target β-strand has a hydroxyl-containing side chain, then the first residue of the β-strand-forming section of peptide should also have a hydroxyl-containing side chain; if the first residue of the aggregation-causing segment of the target β-strand has a basic side chain, then the first residue of the β-strand-forming section of peptide should have an acidic side chain; and if the first residue of the aggregation-causing segment of the target β-strand has an acidic side chain, then the first residue of the β-strand-forming section of peptide should have a basic side chain. This selection procedure is continued for all the remaining side chains in the β-strand-forming section of peptide.

In general, a suitable sequence of side chains in the β-strand-forming section of peptide can also be taken directly from the section of the β-strand which undesirably associates with the aggregation-causing section of the target β-strand. For example, the Alzheimer's Aβ peptide aggregates into insoluble β-fibres by the intermolecular association of identical KLVFF (SEQ ID NO: 1) aggregation-causing segments of peptide as β-strands in the antiparallel orientation, and in the resulting antiparallel β-sheet complex, the four hydrophobic side chains of each β-strand form hydrophobic interactions with those of the associated β-strand, while the basic lysine side chain of each β-strand presumably forms an electrostatic interaction with one of the two acidic side chains that follow the KLVFF sequence (SEQ ID NO: 1) in the associated β-strand (Tjernberg et al., 1997). Since the β-strand-forming section of peptide is designed to associate as a β-strand with the KLVFF sequence (SEQ ID NO: 1) in the parallel orientation, the sequence of its side chains is preferably designed to be homologous or identical to the KLVFF sequence (SEQ ID NO: 1) in reverse order, i.e. FFVLK (SEQ ID NO: 3. Other compounds or compositions corresponding to the present invention may be designed to associate specifically with other target β-strands by a similar method.

The de novo design of β-sheet polypeptides has been described in the art. For example, reference is made to Smith and Regan, (1995); Smith and Regan, (1997); De Alba et al., (1999); and Kortemme et al., (1998). These and other approaches may be employed in designing a suitable polypeptide. For instance, a suitable sequence of side chains in the β-strand-forming section of peptide may be determined by constructing a molecular model of a parallel or antiparallel β-sheet complex in which the target β-strand is associated with a second β-strand, and then adapting the identity and conformation of the side chains of the second β-strand to make favourable non-covalent interactions with the side chains of the target β-strand. This may be done using a computer and appropriate software as follows:

First, a molecular model of the target β-strand is constructed. This may be done by extracting the coordinates of a β-strand in a protein of known molecular structure, and then changing the sequence of its side chains to that of the target β-strand. Next, a molecular model of a second β-strand is constructed by a similar method, is transformed into its own mirror image and is then positioned alongside either edge of the target β-strand in the parallel or antiparallel orientation to form a two-stranded parallel or antiparallel β-sheet complex. Possible side chains for each consecutive residue in the second β-strand are then considered, and their alternative conformations are explored to determine whether they are likely to form favourable non-covalent interactions with the neighbouring side chains of the associated target β-strand in the β-sheet complex. Finally, once a suitable sequence of side chains is selected, energy-minimisation and molecular dynamics programs may be applied to investigate the theoretical validity of the model, before synthesising the candidate peptide and testing it experimentally for activity.

Other guidance relating to the design of peptides which form β-strands may be found in the foregoing material relating to β-sheet propensities for amino-acids, as well as the following sources: Nelsoney and Kelly, (1996); Hutchinson et al., (1998); Pham et al., (1998); Minor and Kim, (1996); Koepf et al., (1999); and Minor and Kim, (1994b).

Selection and Location of Nα-Substituents

In order that the Nα-substituents of the Nα-substituted α-D-amino acid residues in the β-strand-forming section of peptide lie along only one of the two edges of the β-strand formed by the β-strand-forming section of peptide, the Nα-substituted α-D-amino acid residues are interspersed by odd numbers of unsubstituted amino-acids, unless there is only one Nα-substituted α-D-amino acid residue in the β-strand-forming section of peptide, because the repeating unit of a β-strand is two residues: if any two Nα-substituted α-D-amino acid residues in the β-strand-forming section of peptide were adjacent or separated by an even number of unsubstituted residues, then their Nα substituents would lie on opposite edges of the β-strand, and neither edge of the β-strand would be able to associate with a target β-strand and thereby sterically hinder the association of other β-strands with that target β-strand.

In theory, therefore, the Nα-substituted α-D-amino acid residues in the β-strand-forming section of peptide could be very large numbers of residues apart, or there could be only one Nα-substituted α-D-amino acid residue in the β-strand-forming section of peptide. In practice, however, successive Nα-substituted α-D-amino acid residues in the β-strand-forming section of peptide should preferably be separated by no more than 3 unsubstituted residues because the steric constraints imposed by these residues actually serve to encourage the β-strand-forming section of peptide to adopt the active β-strand conformation (Manavalan and Momany, 1980).

In the most preferable case therefore, successive Nα-substituted amino acid α-D-amino acid residues in the β-strand-forming section of peptide are separated from each other by single unsubstituted residues so that the β-strand-forming section of peptide comprises a sequence of alternating Nα-substituted and Nα-unsubstituted α-D-amino acid residues. This induces the entire section of peptide to adopt an active β-strand conformation.

The Nα-substituents may be substantially any atom or group that is larger than a hydrogen atom, which essentially means any atom or group other than a hydrogen atom. However, they must also not sterically prevent the β-strand-forming section of peptide from forming a β-strand, because the β-strand-forming section of peptide has to form a β-strand in order to associate with a target β-strand.

The Nα-substituent is thus optionally a fluorine atom or a hydroxy group, or another group that is connected to the Nα atom by an oxygen atom within it, such as a methoxy group or another alkoxy group.

Preferably, the Nα-substituent is a group that is connected to the Na atom by a methylene ($CH_2$) group within it. Such a group can be incorporated into the β-strand-forming section of peptide by standard methods of solution- or solid-phase peptide synthesis, and the connecting methylene group is sterically compatible with the formation of a β-strand. Suitable examples of this preferred form of Nα-substituent include a methyl or ethyl group, or another alkyl or aliphatic group that is connected to the Nα atom by a methylene ($CH_2$) group within it, or a substituted or unsubstituted benzyl group, such as an acetylated or otherwise acylated 2-hydroxy-4-methoxybenzyl (AcHmb) group, or another aryl-methyl group.

A methyl group is the most preferred form of Nα-substituent because it is the simplest group that can be incorporated into the β-strand-forming section of peptide by standard methods of solution- or solid-phase peptide synthesis, and the corresponding amino-acids and their Fmoc and Boc derivatives are commercially available.

The 2-hydroxy-4-methoxybenzyl (AcHmb) group is a further preferred form of Nα-substituent because the corresponding amino-acids and their Fmoc and Boc derivatives are also commercially available, but this group is fairly labile unless its 2-hydroxyl group is acetylated or otherwise acylated (Quibell et al., 1995; Quibell et al., 1995; Quibell et al., 1994).

The 2-hydroxybenzyl (AcHb) group is yet another preferred form of Nα-substituent, and unlike the 2-hydroxy-4-methoxybenzyl group, it does not need to be acetylated or otherwise acylated (Johnson and Quibell, 1994).

The β-strand-forming propensity of the β-strand-forming section of peptide may be increased further by including Nα-substituted or Nα-unsubstituted α-D-amino acid residues whose side chains sterically favour the β-strand conformation. These include α-D-amino acid residues with β-branched side chains, such as α-D-threonine, α-D-valine, α-D-isoleucine, α-D-tert-leucine, α-D-p-hydroxyvaline, and their Nα-substituted derivatives. Other α-D-amino acid residues which favour the β-strand conformation, for example those with aromatic side chains such as α-D-tyrosine, α-D-phenylalanine and α-D-tryptophan, and those with aliphatic hydrophobic side chains such as α-D-leucine and α-D-methionine, plus α-D-serine and α-D-glutamine, should also be included in the β-strand-forming section of peptide if and where appropriate: they must be compatible with the chemistry of solution- or solid-phase peptide synthesis, they must not sterically hinder the association of the free edge of the β-strand formed by the β-strand-forming section of peptide with the target β-strand, and they should preferably promote the β-strand formed by the β-strand-forming section of peptide to associate tightly with the target β-strand.

As explained above, the Nα-substituted and Nα-unsubstituted α-D-amino acid residues in the β-strand-forming section of peptide should preferably promote the β-strand-forming section of peptide to form a β-strand; but they should also preferably promote this β-strand to associate as tightly as possible with the target β-strand. For this, their side chains should form strong non-covalent interactions with the neighbouring side chains of the target β-strand when the two strands are associated with each other in the parallel or antiparallel β-sheet complex. The strongest non-covalent interactions that can exist between the neighbouring side chains of associated β-strands in aqueous solutions are hydrophobic interactions between hydrophobic side chains and hydrogen bonds between amide-containing side chains. The segment of the target β-strand most responsible for its aggregation is likely to be rich in residues which have these side chains, and therefore it is this aggregation-causing segment of the target β-strand with which the β-strand-forming section of peptide can potentially associate most tightly. For this reason, most of the Nα-substituted and Nα-unsubstituted α-D-amino acid residues in the β-strand-forming section of peptide preferably have hydrophobic or amide-containing side chains. The preferred amino-acid residues with hydrophobic side chains include α-D-valine, α-D-leucine, α-D-isoleucine, α-D-methionine, α-D-phenylalanine, α-D-tyrosine, α-D-tryptophan, and their Nα-substituted derivatives; while the preferred amino-acid residues with amide-containing side chains include α-D-asparagine, α-D-glutamine, and their Nα-substituted derivatives. The most preferred side chain of each residue in the β-strand-forming section of peptide depends on the neighbouring side chain of the associated target β-strand in the β-sheet complex, because their stereochemistries must be compatible with the formation of a favourable non-covalent interaction between them. In general, however, the most preferred hydrophobic side chain is that of leucine because it is fairly large but relatively flexible, being able to adopt any one of nine different rotamer conformations, and can easily adapt its stereochemistry to make the most favourable hydrophobic interaction with almost any neighbouring hydrophobic side chain of an associated target β-strand; the most preferred amide-containing side chain is that of glutamine because it too is relatively flexible, and is more likely to be able to make a favourable hydrogen bond with a neighbouring glutamine or asparagine side chain of an associated target β-strand. However, any hydrophobic side chain, or side chain which has a considerable hydrophobic portion, could be included in the β-strand-forming section of peptide, as could any amide-containing side chain, as long as they did not sterically hinder the β-strand-forming section of peptide from forming a β-strand, or from associating as such with a target β-strand.

Although most of the Nα-substituted and Nα-unsubstituted α-D-amino acid residues in the β-strand-forming section of peptide should have hydrophobic or amide-containing side chains, the remainder of the Nα-substituted and Nα-unsubstituted α-D-amino acid residues in the β-strand-forming section of peptide may have side chains which are neither hydrophobic nor amide-containing, but which can nevertheless form favourable non-covalent interactions with the neighbouring side chains of an associated β-strand. For example: the acidic side chains of aspartate and glutamate may form salt bridges with the basic side chains of histidine, arginine, and lysine in an associated β-strand, and conversely, the basic side chains of histidine, arginine, and lysine may form salt bridges with the acidic side chains of aspartate and glutamate in an associated β-strand; the hydroxyl-containing side chains of serine, threonine, and β-hydroxyvaline may form hydrogen bonds with the neighbouring hydroxyl-containing side chains of an associated β-strand.

Prevention of β-Sheet Stacking

In order that the β-sheets formed by association of the β-strands do not aggregate by stacking, the β-strand-forming section of peptide also preferably includes one or more α-D-amino acid residues having a side chain which extends beyond the neighbouring side chains in the β-strand formed by the β-strand-forming section of peptide. Such an extended side chain is preferably long and preferably has a polar end, so that it does not support the stacking of β-sheets. The side chains of lysine and arginine are suitable examples of such extended side chains having a polar end.

Labelling of Peptides

In order that the peptides according to the invention can be traced or detected, the β-strand-forming section of peptide may include an α-D-amino acid residue having a side chain which contains a radioactive or magnetically active nucleus, such as an α-D-phenylalanine, α-D-tyrosine, or α-D-thyronine residue with one or more radioactive or magnetically active iodine or other halogen atoms substituted onto the aromatic ring(s); or the β-strand-forming section of peptide may include an α-D-amino acid residue having a side chain which contains a fluorescent, coloured, or other spectroscopically detectable group, including spin labels such as the 2,2,5,5-tetramethyl-1-pyrrolidinyloxy (PROXYL) and 2,2,6,6-tetramethyl-1-piperidinyloxy (TEMPO) groups which contain unpaired electrons. A peptide containing such a spectroscopically detectable group or a radioactive or magnetically active nucleus may be used as a traceable probe to indicate the presence and location of target β-strands or insoluble β-fibres, either in vitro or in vivo.

Membrane Penetration

In order that the compound or composition can more easily penetrate cell membranes and the blood-brain barrier, the β-strand-forming section of peptide preferably contains a high proportion of amino-acid residues having hydrophobic or basic side chains. The hydrophobic side chains interact with the hydrophobic portions of the phospholipid molecules which constitute these barriers, while the basic side chains might interact with the phosphate head groups of these molecules, just as the basic side chains in the membrane-penetrating peptide segments of the Drosophila Antennapedia homeodomain and the HIV-1 Tat protein have been proposed to do (Derossi et al., 1996; Vives et al., 1997; Vives et al., 1997).

Alternatively, or in addition to the foregoing, the peptide of the invention may be encouraged to penetrate cell membranes and the blood-brain barrier more easily by arranging the β-strand-forming section of peptide such that it is preceded or followed in the peptide sequence by, or otherwise attached to, a distinct membrane-penetrating section of peptide that consists entirely or almost entirely of amino-acid residues having basic or hydrophobic side chains. These membrane-penetrating sections of peptide are able to carry peptides and small proteins to which they are attached through cell membranes and the blood-brain barrier by interacting with the phospholipid molecules which constitute these biological barriers, as described above. Other sections of peptide which are rich in residues with basic and/or hydrophobic side chains may also be able to act as vectors for carrying the β-strand-forming section of peptide through these barriers (Derossi et al., 1998). The side chain of each residue in the membrane-penetrating section of peptide is preferably a basic or hydrophobic group, such as those of alanine, valine, leucine, isoleucine, methionine, phenylalanine, tyrosine, tryptophan, proline, histidine, lysine, and arginine. The membrane-penetrating section of peptide may also include α-D- or Nα-substituted amino-acid residues to make it more resistant to enzyme-catalysed proteolytic degradation.

The membrane-penetrating section of peptide may be attached to the β-strand-forming section of peptide by including it in the solid-phase synthesis of the β-strand-forming section of peptide as one continuous peptide, wherein the membrane-penetrating section of peptide either precedes or follows the β-strand-forming section of peptide. Alternatively, the membrane-penetrating section of peptide may be attached via an amide or disulphide bond to one of the side chains of the β-strand-forming section of peptide.

The β-strand-forming section of peptide may have a free, acetylated, or otherwise acylated N terminus and/or a free, amidated, or esterified C terminus, or may form part of a larger peptide which has a free, acetylated, or otherwise acylated N terminus and/or a free, amidated, or esterified C terminus. Amidation or esterification of the C terminus is preferable because a free carboxyl group reduces the ability of a peptide to penetrate cell membranes and the blood brain barrier, due to unfavourable electrostatic interactions between this negatively charged group and the negatively charged phosphate head groups of the phospholipid molecules which constitute these barriers.

Acetylation or acylation of the N-terminal amino group may actually reduce the ability of the peptide to penetrate cell membranes and the blood brain barrier because a free positively charged N-terminal amino group would form favourable electrostatic interactions with the negatively charged phosphate head groups of the phospholipid molecules, and thereby help the peptide to cross these barriers.

However, a free positively charged N-terminal amino group would not form as strong a hydrogen bond with the backbone carbonyl oxygen atom of an associated target β-strand as an acetylated or otherwise acylated N-terminal amino group would. Therefore, an acetylated or otherwise acylated N-terminal amino group is preferred if the N-terminal amino group forms part of the β-strand-forming section of peptide: the problem of reduced ability of the peptide to penetrate cell membranes and the blood-brain barrier can be overcome by attaching residues with basic side chains or a distinct membrane-penetrating section of peptide to either end of the β-strand-forming section of peptide, as described above.

Attachment of Functional Groups

The peptide according to the invention may be attached to a functional component. This functional component may be a section of peptide or other molecule which causes the compound or composition to target specific organs, cells, or molecules, such as a hormone, antibody, transcription factor, or other protein molecule; or it may be a label as described above, such as an atom or group that contains a radioactive or magnetically active nucleus; or it could be a fluorescent, coloured, or other spectroscopically detectable group; or it could be a group which contains an unpaired electron and thereby acts as a spin label, such as the 2,2,5,5-tetramethyl-1-pyrrolidinyloxy (PROXYL) group or the 2,2,6,6-tetramethyl-1-piperidinyloxy (TEMPO) group; or it may be an enzyme, or a cytotoxic molecule which selectively kills cells containing or otherwise associated with the target β-strand; or it may be a solid matrix, resin, or support.

The β-strand-forming section of peptide is attached to any of these functional components or some other functional component by means of an amide bond, ester bond, or any other suitable linkage between a side chain, Nα-substituent, or either end of the full peptide. The functional component, and this linkage is made before, during, or after synthesis of the full peptide by coupling the appropriate molecules. For example, the inclusion of a cysteine or lysine residue in the full peptide allows it to be attached to a functional component that contains an electrophilic group such as a bromo or iodo group, or an ester or anhydride group, by means of the nucleophilic attack of the thiol sulphur atom of the cysteine residue or the amino nitrogen atom of the lysine residue on that electrophilic group of the functional component. Alternatively, a bifunctional cross-linking agent may be used to attach the β-strand-forming section of peptide to the functional component; or the full peptide may be synthesised using a specially prepared amino-acid derivative which already contains the functional component; or a standard coupling agent such as dicyclohexylcarbodiimide may be used to form an amide bond between a side-chain or terminal carboxyl or amino group of the peptide and an amino or carboxyl group of the functional component.

Uses of Peptides According to the Invention

The chemical compounds and compositions described herein can be used for any application which employs their ability to associate specifically with target β-strands and thereby inhibit the association of other β-strands with those target β-strands. One application for these compounds is in their use to inhibit or reverse the aggregation of proteins or peptides into insoluble β-fibres, or more specifically, to inhibit or reverse the association of β-strands into β-sheets, in vitro or in vivo. In vitro, for example, they can be used in combination with an additional agent such as urea, guanidinium chloride, or another denaturant to assist in the refolding of denatured, misfolded, or aggregated proteins or peptides.

According to the present aspect of the invention, the denatured, misfolded, or aggregated protein or peptide is dialysed from a solution containing the peptide according to the invention plus the additional agent, for example, or by protein-renaturation chromatography through a solid matrix, resin, or support to which the peptide is covalently attached, in the presence of the additional agent.

The peptides are also useful in vivo or in vitro for the diagnosis, study, or treatment of diseases caused by the aggregation of proteins or peptides into insoluble β-fibres, such as those listed in the introduction. For such applications, the compounds are designed so that they can penetrate cell membranes and the blood-brain barrier, and so that they are resistant to enzyme-catalysed proteolysis; a traceable group may also be incorporated into the invented compound as described so that it may be used as a probe for the diagnosis of these diseases.

The peptides of the invention could also be used either in vitro or in vivo to inhibit the oligomerisation or association of protein subunits where this occurs by the association of β-strands. Many enzymes and other proteins are active only as dimers or other oligomers which are formed from individual subunits by the association of β-strands, and the invented compounds could be used to inhibit the activity of these proteins by binding to these β-strands and thereby hindering their association to form the complete protein complex. For example, the catalytic activity of the HIV protease depends on its dimerisation, which involves the association of β-strands formed by its N- and C-terminal sections of peptide. Short peptides homologous to these sections of peptide have been successfully used to inhibit the dimerisation and thereby the catalytic activity of this enzyme (Babe et al., 1992; Franciskovich et al., 1993; Schramm et al., 1993; Schramm et al., 1996; Schramm et al., 1992; Zutshi et al., 1997). These peptides are, however, not very soluble in aqueous solutions and are susceptible to degradation by proteolytic enzymes because they consist solely of Nα-unsubstituted α-L-amino-acid residues, therefore they are not suitable for use as therapeutic agents. The compounds described herein are more soluble in aqueous solutions and are resistant to degradation by proteolytic enzymes, so they are more suitable for use as therapeutic agents. For a review on the use of 'interface' peptides to inhibit the oligomerisation or association of protein subunits into active complexes, see reference (Zutshi et al., 1998).

Thus the ability of the peptides of the invention to inhibit the association of β-strands may be used for any application both in vitro and in vivo. In addition, the ability of these compounds to simply associate specifically with target β-strands may also be used as such for any in vitro or in vivo application. For example, the compounds could be used as a traceable probe, especially as a histochemical stain or indicator, to indicate the presence or location of β-strands, β-sheets, or β-fibres in vitro or in vivo. In such applications, the compound contains or is attached to an atom or group that contains a radioactive or magnetically active nucleus, or a fluorescent, coloured, or other spectroscopically detectable group such as a group which contains an unpaired electron and thereby acts as a spin label. Specifically, such a compound may be used as a histochemical stain or indicator to monitor the production of insoluble β-fibres in patients of Alzheimer's Disease and other neurodegenerative diseases caused by the aggregation of proteins or peptides into insoluble β-fibres in the brain.

The peptides according to the invention may be attached to a solid matrix, resin, or support and used as such for protein-renaturation chromatography as described above; they could also be used in this form for affinity chromatography wherein the β-strand-forming section of peptide acts as a bait to capture the proteins or peptides which form the target β-strand. For example, a β-strand-forming section of peptide designed to form a β-strand and associate specifically as such with a target β-strand formed by a particular protein of biochemical interest could be attached to a solid matrix, resin, or support to enable purification of that particular protein by affinity chromatography: the protein which contains the target β-strand will bind to the β-strand formed by the β-strand-forming section of peptide attached to the solid support, and may thereby be separated from other proteins which will not be recognised by the β-strand-forming section of peptide; the purified protein may then be liberated from the support by adding a free form of the β-strand-forming section of peptide, or some other agent which disrupts the interaction between the two β-strands, such as urea or some other denaturant.

Finally, the compounds described herein may be included in a combinatorial library of such compounds to screen for one particular compound which is to be used for any of the above applications. This combinatorial library could be prepared by any suitable standard method of preparing synthetic peptide libraries (Lebl and Krchnak, 1997), wherein Nα-substituted α-D-amino acid residues are included in the peptides at appropriate positions according to the present invention. The resulting library is then screened for peptides which bind to a target β-strand sufficiently tightly, or which sufficiently inhibit the activity of an oligomeric protein by blocking its oligomerisation, or which rescue cells that would otherwise be killed by the aggregation of proteins or peptides into insoluble β-fibres. The selected compounds may be used directly for any of the above applications, or used to design combinatorial libraries of compounds which are even more active, or which are more suitable for use as therapeutic agents.

For use as therapeutic agents, the peptides according to the invention may be formulated according to established practices. The peptide according to the invention may be administered in a convenient manner such as by the oral, intravenous (where water soluble), intramuscular, subcutaneous, intranasal, intradermal or suppository routes or implanting (e.g. using slow release molecules). Depending on the route of administration, the peptide may be required to be coated in a material to protect it from the action of enzymes, acids and other natural conditions which may inactivate it.

In order to administer the peptide by other than parenteral administration, it may be coated by, or administered with, a material to prevent its inactivation. For example, the peptide may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include those of pancreatic trypsin and other digestive proteases.

Liposomes include water-in-oil-in-water CGF emulsions as well as conventional liposomes.

The active compound may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene gloycol, and the like), suitable mixtures thereof, and vegetable oils. The proper fluidity can be maintained, for example, by the use of a coating such as lecithin, by the maintenance of the required particle size in the case of dispersion and by the use of superfactants.

The prevention of the action of microorganisms can be brought about by various antibacterial and antifungal agents, for example, parabens, chlorobutanol, phenol, sorbic acid, thirmerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilisation. Generally, dispersions are prepared by incorporating the sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the peptide is suitably protected as described above, it may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. The amount of active compound in such therapeutically useful compositions is such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such as active material for the treatment of disease in living subjects having a diseased condition in which bodily health is impaired.

The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

The present invention provides the use of a peptide according to the invention for the manufacture of a medicament for the treatment of disease associated with aberrant protein/polypeptide structure. The aberrant nature of the protein/polypeptide may be due to misfolding or unfolding which in turn may be due to an anomalous e.g. mutated amino-acid sequence. The protein/polypeptide may be destabilised or deposited as plaques e.g. as in Alzheimer's disease. The disease might be caused by a prion. A polypeptide-based medicament of the invention would act to renature or resolubilise or inhibit the accumulation of aberrant, defective or deposited proteins.

The invention is further described, for the purposes of illustration only, in the following examples.

EXAMPLE 1

Aggregation of the Alzheimer's Aβ peptide into amyloid fibres is caused by the intermolecular association of five-residue KLVFF (SEQ ID NO: 1) peptide segments comprising residues 16–20 of the Aβ peptide (Tjernberg et al., 1997). A peptide, referred to below as Peptide X (SEQ ID NO: 2), was therefore constructed to associate tightly with the KLVFF motif (SEQ ID NO: 1), in order to inhibit aggregation of the Aβ peptide.

The sequence of side chains in Peptide X is LLLLRR (SEQ ID NO: 2), which is highly homologous to the reverse sequence FFVLK (SEQ ID NO: 3), except that an additional residue having an arginine side chain has been added to the C-terminus.

Leucine side chains were selected to take the place of all four hydrophobic side chains in the FFVLK sequence (SEQ ID NO: 3) because they are relatively flexible and can adapt their conformation to make strong hydrophobic interactions with the neighbouring hydrophobic side chains of an associated β-strand, while an arginine side chain was chosen to take the place of the lysine side chain in the FFVLK sequence (SEQ ID NO: 3) because it can form a stronger electrostatic interaction with one of the two acidic side chains which follow the aggregation-causing KLVFF (SEQ ID NO: 1) segment of the target β-strand.

The additional residue having an arginine side chain at the C-terminus of Peptide X (SEQ ID NO: 2) may form another strong electrostatic interaction with the second of these two acidic side chains, and should further assist Peptide X (SEQ ID NO: 2) to penetrate cell membranes and the blood-brain barrier.

Finally, the N-terminal amino group of Peptide X (SEQ ID NO: 2) was acetylated to maximise its association with the aggregation-causing KLVFF segment (SEQ ID NO: 1) of the target β-strand, and its otherwise negatively charged C-terminal carboxyl group was amidated to further improve the ability of Peptide X (SEQ ID NO: 2) to penetrate cell membranes and the blood-brain barrier. In this way, Peptide X (SEQ ID NO: 2) has been designed to associate specifically as a β-strand with the aggregation-causing KLVFF (SEQ ID NO: 1) segment of the target β-strand formed by the Alzheimer's Aβ peptide to form an parallel β-sheet complex, thereby sterically hindering the aggregation of the Aβ peptide into insoluble β-fibres.

Peptide X (SEQ ID NO: 2) is a substituted peptide, in accordance with the present invention. The sequence, including substituents, is Nα-acetyl-(D-leucine)-(Nα-methyl-D-leucine)-(D-leucine)-(Nα-methyl-D-leucine)-(D-arginine)-(D-arginine)-NH$_2$, or all-D-[Ac-Leu-meLeu-Leu-meLeu-Arg-Arg-NH$_2$.

Peptide X (SEQ ID NO: 2) was synthesised by 9-fluorenylmethoxycarbonyl- (Fmoc-) based solid-phase peptide synthesis (Fields and Noble, 1990) using the coupling agent 1-hydroxy-7-azabenzotriazole (HOAt), which is able to couple sterically hindered amino-acid residues (Angell et al., 1994; Carpino et al., 1994).

Peptide X (SEQ ID NO: 2) was found to be completely soluble in aqueous solutions over a wide range of pH values, even at a concentration of 10 mM (about 10 mg/ml); yet, except for the two positively charged arginine side chains, it is extremely hydrophobic and is therefore able to penetrate cell membranes and the blood-brain barrier, especially as it is only six amino-acid residues in length. The two positively charged arginine side chains assist the peptide to penetrate cell membranes and the blood-brain barrier by making electrostatic interactions with the negatively charged phosphate head groups of their constituent phospholipid molecules, resulting in the formation of inverted micelles which carry the peptide molecules across these membranes.

The capacity of Peptide X (SEQ ID NO: 2) to inhibit the aggregation of a synthetic peptide fragment corresponding to residues 11 to 25 of the Alzheimer's Aβ peptide into amyloid fibrils was determined quantitatively using a standard assay based on the amyloid-dependent fluorescence of thioflavin T at 482 nm (Levine, 1993).

Peptide X (SEQ ID NO: 2) was dissolved in water to a concentration of 10 mM (about 10 mg/ml). Alzheimer's Aβ peptide fragment, at a concentration of 50/M (about 0.1 mg/ml) in 50 mM sodium acetate buffer (pH 5.0), was incubated at 25° C. in the absence or presence of Peptide X (SEQ ID NO: 2) at concentrations ranging from 100 µM to 1 mM; the aggregation of the Aβ peptide fragment into insoluble β-fibres in the solutions was determined quantitatively after 20 minutes by measuring the fluorescence of 1%M added thioflavin T at 482 nm using an excitation wavelength of 440 nm. 5 ml aliquots of these solutions were then analysed by electron microscopy to confirm that Peptide X (SEQ ID NO: 2) had inhibited and/or reversed the aggregation of the Alzheimer's Aβ peptide fragment into insoluble β-fibres.

Figure 6:
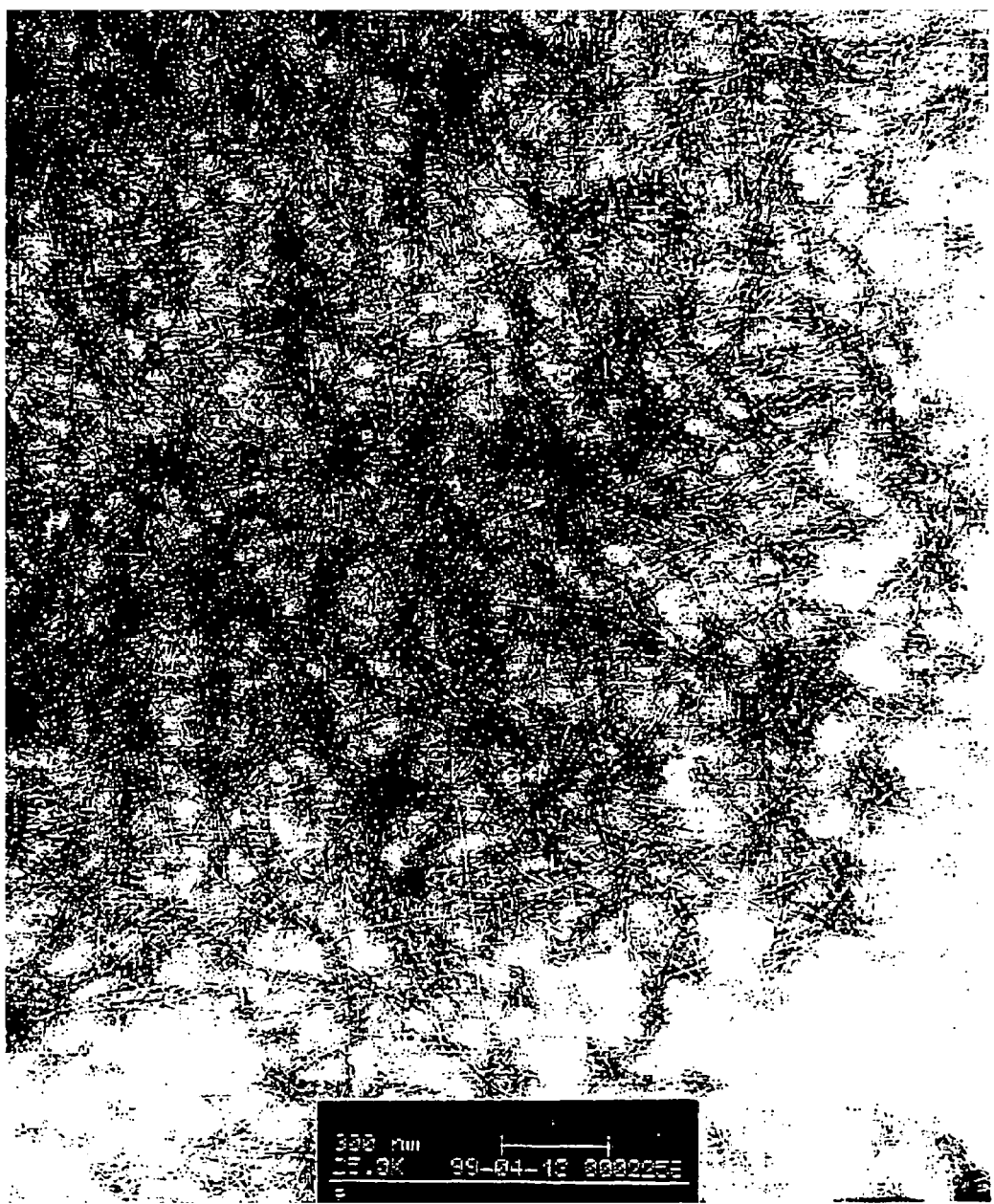
FIG. 6 is an electron micrograph showing aggregated Alzheimer's Aβ peptides. Alzheimer's Aβ peptide was incubated at a concentration of 500 mM and the aggregate examined by electron microscopy.
Figure 7:
FIG. 7 is an electron micrograph showing Alzheimer's Aβ peptides incubated at a concentration of 500 mM in the presence of Peptide X SEQ ID NO: 2); electron microscope examination shows a substantial elimination of aggregation.

According to this assay, the aggregation of the Aβ peptide fragment into amyloid fibrils was inhibited by more than 60% in the presence of 200 µM Peptide X (SEQ ID NO: 2) (see FIG. 5). Similar results were obtained when Peptide X (SEQ ID NO: 2) was added to the Aβ peptide fragment after incubation, showing that Peptide X (SEQ ID NO: 2) is able to disaggregate preformed amyloid fibrils. Analysis of the Aβ peptide fragment incubated with and without 500 mM Peptide X (SEQ ID NO: 2) by electron microscopy confirmed that Peptide X (SEQ ID NO: 2) had almost completely inhibited aggregation of the Aβ peptide fragment into amyloid fibrils (see FIGS. 6 and 7).

FIGS. 3 and 4 show how Peptide X (SEQ ID NO: 2) forms a β-strand (X) and associates as such with one edge of a target β-strand (Y) formed by a segment of the Aβ peptide or some other peptide-based molecule in either orientation to form a parallel (FIG. 3) or antiparallel (FIG. 4) two-stranded β-sheet complex, thereby sterically hindering the association of other β-strands with that edge of the target β-strand.

The entire length of Peptide X (SEQ ID NO: 2) is able to form a β-strand because it consists solely of α-D-amino acid residues which sterically permit it to do so: they are all able to adopt the respective phi and psi angles required to form a β-strand. Furthermore, the steric constraints imposed by the Nα-methyl groups of the two Nα-methyl-α-D-amino acid residues (residues 2 and 4) serve to encourage Peptide X (SEQ ID NO: 2) to form a β-strand. When Peptide X (SEQ ID NO: 2) does form a β-strand, these two Nα-methyl groups lie along the same edge of the β-strand, as shown in either FIG. 3 or FIG. 4, because they are an even numbers of residues (in this case two residues) apart from each other and the repeating unit of a β-strand is two residues. This edge of the β-strand formed by Peptide X (SEQ ID NO: 2) is sterically hindered by these two Nα-methyl groups from associating with another β-strand. The other edge of the β-strand formed by Peptide X (SEQ ID NO: 2), however, remains free to do so, and can associate in either the parallel or antiparallel orientation with a free edge of a target β-strand formed by a segment of the Aβ peptide or some other protein or peptide molecule to form a parallel (FIG. 3) or antiparallel (FIG. 4) two-stranded β-sheet complex, thereby sterically hindering the association of other β-strands with that edge of the target β-strand, and thus preventing the formation of extended β-sheets and the deposition of insoluble pathogenic β-fibres. This association of the β-strand formed by Peptide X (SEQ ID NO: 2) with the target β-strand is made by hydrogen bonds between their backbone peptide groups and additional non-covalent interactions between their side chains.

REFERENCES

Angell, Y. M., Garciaecheverria, C., and Rich, D. H. (1994). Comparative-Studies of the Coupling of N-Methylated, Sterically Hindered Amino-Acids During Solid-Phase Peptide-Synthesis. Tetrahedron Letters 35, 5981–5984.

Arima, K., Ueda, K., Sunohara, N., Hirai, S., Izumiyama, Y., TonozukaUehara, H., and Kawai, M. (1998). Immuno-electron-microscopic demonstration of NACP/alpha-synuclein-epitopes on the filamentous component of Lewy bodies in Parkinson's disease and in dementia with Lewy bodies. Brain Research 808, 93–100.

Baba, M., Nakajo, S., Tu, P. H., Tomita, T., Nakaya, K., Lee, V. M. Y., Trojanowski, J. Q., and Iwatsubo, T. (1998). Aggregation of alpha-synuclein in Lewy bodies of sporadic Parkinson's disease and dementia with lewy bodies. American Journal of Pathology 152, 879–884.

Babe, L. M., Rose, J., and Craik, C. S. (1992). Synthetic Interface Peptides Alter Dimeric Assembly of the Hiv-1 and Hiv-2 Proteases. Protein Science 1, 1244–1253.

Bai and Englander, (1994) Proteins: Structure, Function and Genetics 18:262–266.

Bandiera, T., Lansen, J., Post, C., and Varasi, M. (1997). Inhibitors of A beta peptide aggregation as potential anti-Alzheimer agents. Current Medicinal Chemistry 4, 159–170.

Benson, M. D., and Uemichi, T. (1996). Transthyretin amyloidosis. Amyloid-International Journal of Experimental and Clinical Investigation 3, 44–56.

Bronfman, F. C., Garrido, J., Alvarez, A., Morgan, C., and Inestrosa, N.C. (1996). Laminin inhibits amyloid-beta-peptide fibrillation. Neuroscience Letters 218, 201–203.

Burgevin, M. C., Passat, M., Daniel, N., Capet, M., and Doble, A. (1994). Congo-Red Protects Against Toxicity of Beta-Amyloid Peptides On Rat Hippocampal-Neurons. Neuroreport 5, 2429–2432.

Camilleri, P., Haskins, N.J., and Howlett, D. R. (1994). Beta-Cyclodextrin Interacts With the Alzheimer Amyloid Beta-A4 Peptide. Febs Letters 341, 256–258.

Carpino, L. A., Elfaham, A., Minor, C. A., and Albericio, F. (1994). Advantageous Applications of Azabenzotriazole (Triazolopyridine)- Based Coupling Reagents to Solid-Phase Peptide-Synthesis. Journal of the Chemical Society-Chemical Communications, 201–203.

Clark, A., Charge, S. B. P., Badman, M. K., and deKoning, E. J. P. (1996). Islet amyloid in type 2 (non-insulin-dependent) diabetes. Apmis 104, 12–18.

De Alba et al., (1999) Protein Science 8:854–865.

Derossi, D., Calvet, S., Trembleau, A., Brunissen, A., Chassaing, G., and Prochiantz, A. (1996). Cell internalisation of the third helix of the antennapedia homeodomain is receptor-independent. Journal of Biological Chemistry 271, 18188–18193.

Derossi, D., Chassaing, G., and Prochiantz, A. (1998). Trojan peptides: the penetratin system for intracellular delivery. Trends in Cell Biology 8, 84–87.

Derossi, D., Joliot, A. H., Chassaing, G., and Prochiantz, A. (1994). The 3rd Helix of the Antennapedia Homeodomain Translocates Through Biological-Membranes. Journal of Biological Chemistry 269, 10444–10450.

Doig, A. J. (1997). A three stranded beta-sheet peptide in aqueous solution containing N- methyl amino-acids to prevent aggregation. Chemical Communications, 2153–2154.

Fields, G. B., and Noble, R. L. (1990). Solid-Phase Peptide-Synthesis Utilising 9-Fluorenylmethoxycarbonyl Amino-Acids. International Journal of Peptide and Protein Research 35, 161–214.

Forloni, G. (1996). Neurotoxicity of beta-amyloid and prion peptides. Current Opinion in Neurology 9, 492–500.

Forloni, G., Tagliavini, F., Bugiani, O., and Salmona, M. (1996). Amyloid in Alzheimer's disease and prion-related encephalopathies: Studies with synthetic peptides. Progress in Neurobiology 49, 287–315.

Franciskovich, J., Houseman, K., Mueller, R., and Chmielewski, J. (1993). A Systematic Evaluation of the Inhibition of Hiv-1 Protease By Its C-Terminal and N-Terminal Peptides. Bioorganic & Medicinal Chemistry Letters 3, 765–768.

Ghanta, J., Shen, C. L., Kiessling, L. L., and Murphy, R. M. (1996). A strategy for designing inhibitors of beta-amyloid toxicity. Journal of Biological Chemistry 271, 29525–29528.

Hanan, E., and Solomon, B. (1996). Inhibitory effect of monoclonal antibodies on Alzheimer's beta-amyloid peptide aggregation. Amyloid-International Journal of Experimental and Clinical Investigation 3, 130–133.

Horwich, A. L., and Weissman, J. S. (1997). Deadly conformations—Protein misfolding in prion disease. Cell 89, 499–510.

Howlett, D., Cutler, P., Heales, S., and Camilleri, P. (1997). Hemin and related porphyrins inhibit beta-amyloid aggregation. Febs Letters 417, 249–251.

Hughes, S. R., Khorkova, O., Goyal, S., Knaeblein, J., Heroux, J., Riedel, N. G., and Sahasrabudhe, S. (1998). alpha (2)-macroglobulin associates with beta-amyloid peptide and prevents fibril formation. Proceedings of the National Academy of Sciences of the United States of America 95, 3275–3280.

Hutchinson et al., (1998) Protein Science 7:2287–2300.

Joachim, C. L., and Selkoe, D. J. (1992). The Seminal Role of Beta-Amyloid in the Pathogenesis of Alzheimer-Disease. Alzheimer Disease & Associated Disorders 6, 7–34.

Johnson, T., and Quibell, M. (1994). The N-(2-Hydroxybenzyl) Protecting Group For Amide Bond Protection in Solid-Phase Peptide-Synthesis. Tetrahedron Letters 35, 463–466.

Kahn, S. E., Andrikopoulos, S., and Verchere, C. B. (1999). Islet amyloid: A long-recognised but underappreciated pathological feature of type 2 diabetes. Diabetes 48, 241–253.

Kakizuka, A. (1998). Protein precipitation: a common etiology in neurodegenerative disorders? Trends in Genetics 14, 396–402.

Kim and Berg, (1993) Nature 362:267–270.

Koepf et al., (1999) Protein Science 8:841–853.

Kisilevsky, R., and Fraser, P. E. (1997). A beta amyloidogenesis: Unique, or variation on a systemic theme? Critical Reviews in Biochemistry and Molecular Biology 32, 361–404.

Kortemme et al., (1998) Science 281:253–256.

Kudva, Y. C., Hiddinga, H. J., Butler, P. C., Mueske, C. S., and Eberhardt, N. L. (1997). Small heat shock proteins inhibit in vitro A beta (1–42) amyloidogenesis. Febs Letters 416, 117–121.

Lebl, M., and Krchnak, V. (1997). Synthetic peptide libraries. Methods in Enzymology 289, 336–392.

Levine, H. (1993). Thioflavine-T Interaction With Synthetic Alzheimers-Disease Beta-Amyloid Peptides—Detection of Amyloid Aggregation in Solution. Protein Science 2, 404–410.

Lorenzo, A., and Yankner, B. A. (1994). Beta-Amyloid Neurotoxicity Requires Fibril Formation and Is Inhibited By Congo Red. Proceedings of the National Academy of Sciences of the United States of America 91, 12243–12247.

Manavalan, P., and Momany, F. A. (1980). Conformational energy studies on N-methylated analogs of thyrotropin releasing hormone, enkephalin, and leutinising hormone-releasing hormone. Biopolymers 19, 1943–1973.

Merlini, G., Ascari, E., Amboldi, N., Bellotti, V., Arbustini, E., Perfetti, V., Ferrari, M., Zorzoli, I., Marinone, M. G., Garini, P., Diegoli, M., Trizio, D., and Ballinari, D. (1995). Interaction of the Anthracycline 4'-Iodo-4'-Deoxydoxorubicin With Amyloid Fibrils—Inhibition of Amyloidogenesis. Proceedings of the National Academy of Sciences of the United States of America 92, 2959–2963.

Mezey, E., Dehejia, A. M., Harta, G., Suchy, S. F., Nussbaum, R. L., Brownstein, M. J., and Polymeropoulos, M. H. (1998). Alpha synuclein is present in Lewy bodies in sporadic Parkinson's disease. Molecular Psychiatry 3, 493–499.

Miller, S. M., Simon, R. J., Ng, S., Zuckermann, R. N., Kerr, J. M., and Moos, W. H. (1995). Comparison of the Proteolytic Susceptibilities of Homologous L-Amino-Acid, D-Amino-Acid, and N-Substituted Glycine Peptide and Peptoid Oligomers. Drug Development Research 35, 20–32.

Minor and Kim, (1994a) Nature 367:660–663.

Minor and Kim, (1994b) Nature 371:264–267.

Minor and Kim, (1996) Nature 380:730–734.

Miyata, T., Jadoul, M., Kurokawa, K., and DeStrihou, C. V. (1998). beta-2 microglobulin in renal disease. Journal of the American Society of Nephrology 9, 1723–1735.

Nelsoney and Kelly, (1996) Bioorganic and Medicinal Chemistry 4:739–766.

Obrien, T. D., Butler, P. C., Westermark, P., and Johnson, K. H. (1993). Islet Amyloid Polypeptide—a Review of Its Biology and Potential Roles in the Pathogenesis of Diabetes-Mellitus. Veterinary Pathology 30, 317–332.

Pappolla, M., Bozner, P., Soto, C., Shao, H. Y., Robakis, N. K., Zagorski, M., Frangione, B., and Ghiso, J. (1998). Inhibition of Alzheimer beta-fibrillogenesis by melatonin. Journal of Biological Chemistry 273, 7185–7188.

Perutz, M. F. (1999). Glutamine repeats and neurodegenerative diseases: molecular aspects. Trends in Biochemical Sciences 24, 58–63.

Pham et al., (1998) Nature Structural Biology 5:115–119.

Pollack; S. J., Sadler, I. I. J., Hawtin, S. R., Tailor, V. J., and Shearman, M. S. (1995). Sulfonated Dyes Attenuate the Toxic Effects of Beta-Amyloid in a Structure-Specific Fashion. Neuroscience Letters 197, 211–214.

Polymeropoulos, M. H. (1998). Autosomal dominant Parkinson's disease and alpha-Synuclein. Annals of Neurology 44, S63–S64.

Price, D. L., Borchelt, D. R., and Sisodia, S. S. (1993). Alzheimer-Disease and the Prion Disorders Amyloid Beta-Protein and Prion Protein Amyloidoses. Proceedings of the National Academy of Sciences of the United States of America 90, 6381–6384.

Prusiner, S. B., and Dearmond, S. J. (1995). Prion Protein Amyloid and Neurodegeneration. Amyloid-International Journal of Experimental and Clinical Investigation 2, 39–65.

Quibell, M., Packman, L. C., and Johnson, T. (1995). Synthesis of the 3-Repeat Region of Human Tau-2 By the Solid-Phase Assembly of Backbone Amide-Protected Segments. Journal of the American Chemical Society 117, 11656–11668.

Quibell, M., Turnell, W. G., and Johnson, T. (1995). Improved Preparation of Beta-Amyloid(1–43)—Structural Insight Leading to Optimised Positioning of N-(2-Hydroxy-4-Methoxybenzyl) (Hmb) Backbone Amide Protection. Journal of the Chemical Society-Perkin Transactions 1, 2019–2024.

Quibell, M., Turnell, W. G., and Johnson, T. (1994). Reversible Modification of the Acid-Labile 2-Hydroxy-4-Methoxybenzyl (Hmb) Amide Protecting Group—a Simple Scheme Yielding Backbone Substituted Free Peptides. Tetrahedron Letters 35, 2237–2238.

Regan, (–1994) Current Biology 4:656–658.

Ross, C. A. (1997). Intranuclear neuronal inclusions: A common pathogenic mechanism for glutamine-repeat neurodegenerative diseases? Neuron 19, 1147–1150.

Salomon, A. R., Marcinowski, K. J., Friedland, R. P., and Zagorski, M. G. (1996). Nicotine inhibits amyloid formation by the beta-peptide. Biochemistry 35, 13568–13578.

Schramm, H. J., Billich, A., Jaeger, E., Rucknagel, K. P., Arnold, G., and Schramm, W. (1993). The Inhibition of Hiv-1 Protease By Interface Peptides. Biochemical and Biophysical Research Communications 194, 595–600.

Schramm, H. J., Boetzel, J., Buttner, J., Fritsche, E., Gohring, W., Jaeger, E., Konig, S., Thumfart, O., Wenger, T., Nagel, N. E., and Schramm, W. (1996). The inhibition of human immunodeficiency virus proteases by 'interface peptides'. Antiviral Research 30, 155–170.

Schramm, H. J., Breipohl, G., Hansen, J., Henke, S., Jaeger, E., Meichsner, C., Riess, G., Ruppert, D., Rucknagel, K.

P., Schafer, W., and Schramm, W. (1992). Inhibition of Hiv-1 Protease By Short Peptides Derived From the Terminal Segments of the Protease. Biochemical and Biophysical Research Communications 184, 980–985.

Selkoe, D. J. (1994). Cell Biology of the Amyloid Beta-Protein Precursor and the Mechanism of Alzheimers-Disease. Annual Review of Cell Biology 10, 373–403.

Serpell, L. C., Sunde, M., and Blake, C. C. F. (1997). The molecular basis of amyloidosis. Cellular and Molecular Life Sciences 53, 871–887.

Smith et al., (1994) Biochemistry 33:5510–5517.

Smith and Regan, (1995) Science 270:980–982.

Smith and Regan, (1997) Acc. Chem. Res. 30:153–161.

Solomon, B., Koppel, R., Hanan, E., and Katzav, T. (1996). Monoclonal antibodies inhibit in vitro fibrillar aggregation of the Alzheimer beta-amyloid peptide. Proceedings of the National Academy of Sciences of the United States of America 93, 452–455.

Soto, C., Kindy, M. S., Baumann, M., and Frangione, B. (1996). Inhibition of Alzheimer's amyloidosis by peptides that prevent beta-sheet conformation. Biochemical and Biophysical Research Communications 226, 672–680.

Soto, C., Sigurdsson, E. M., Morelli, L., Kumar, R. A., Castano, E. M., and Frangione, B. (1998). beta-sheet breaker peptides inhibit fibrillogenesis in a rat brain model of amyloidosis: Implications for Alzheimer's therapy. Nature Medicine 4, 822–826.

Spillantini, M. G., Crowther, R. A., Jakes, R., Hasegawa, M., and Goedert, M. (1998). alpha-synuclein in filamentous inclusions of Lewy bodies from Parkinson's disease and dementia with Lewy bodies. Proceedings of the National Academy of Sciences of the United States of America 95, 6469–6473.

Sunde, M., and Blake, C. C. F. (1998). From the globular to the fibrous state: protein structure and structural conversion in amyloid formation. Quarterly Reviews of Biophysics 31, 1 (42 pages).

Tjernberg, L. O., Lilliehook, C., Callaway, D. J. E., Naslund, J., Hahne, S., Thyberg, J., Terenius, L., and Nordstedt, C. (1997). Controlling amyloid beta-peptide fibril formation with protease-stable ligands. Journal of Biological Chemistry 272, 12601–12605.

Tjernberg, L. O., Naslund, J., Lindqvist, F., Johansson, J., Karlstrom, A. R., Thyberg, J., Terenius, L., and Nordstedt, C. (1996). Arrest of beta-amyloid fibril formation by a pentapeptide ligand. Journal of Biological Chemistry 271, 8545–8548.

Tomiyama, T., Asano, S., Suwa, Y., Morita, T., Kataoka, K., Mori, H., and Endo, N. (1994). Rifampicin Prevents the Aggregation and Neurotoxicity of Amyloid-Beta Protein in-Vitro. Biochemical and Biophysical Research Communications 204, 76–83.

Trojanowski, J. Q., Goedert, M., Iwatsubo, T., and Lee, V. M. Y. (1998). Fatal attractions: abnormal protein aggregation and neuron death in Parkinson's disease and Lewy body dementia. Cell Death and Differentiation 5, 832–837.

Trojanowski, J. Q., and Lee, V. M. Y. (1998). Aggregation of neurofilament and alpha-synuclein proteins in Lewy bodies—Implications for the pathogenesis of Parkinson disease and Lewy body dementia. Archives of Neurology 55, 151–152.

Verbeek, M. M., Ruiter, D. J., and dewaal, R. M. W. (1997). The role of amyloid in the pathogenesis of Alzheimer's disease. Biological Chemistry 378, 937–950.

Vives, E., Brodin, P., and Lebleu, B. (1997). A truncated HIV-1 Tat protein basic domain rapidly translocates through the plasma membrane and accumulates in the cell nucleus. Journal of Biological Chemistry 272, 16010–16017.

Vives, E., Granier, C., Prevot, P., and Lebleu, B. (1997). Structure-activity relationship study of the plasma membrane translocating potential of a short peptide from HIV-1. Tat protein. Letters in Peptide Science 4, 429–436.

Williams et al., (1987) BBA 916:200–204.

Wilmot and Thornton, (1988) J. Mol. Biol. 203:221–232.

Wisniewski, T., Aucouturier, P., Soto, C., and Frangione, B. (1998). The prionoses and other conformational disorders. Amyloid-International Journal of Experimental and Clinical Investigation 5, 212–224.

Wisniewski, T., Ghiso, J., and Frangione, B. (1997). Biology of A beta amyloid in Alzheimer's disease. Neurobiology of Disease 4, 313–328.

Wood, S. J., MacKenzie, L., Maleeff, B., Hurle, M. R., and Wetzel, R. (1996). Selective inhibition of A beta fibril formation. Journal of Biological Chemistry 271, 4086–4092.

Zutshi, R., Brickner, M., and Chmielewski, J. (1998). Inhibiting the assembly of protein protein interfaces. Current Opinion in Chemical Biology 2, 62–66.

Zutshi, R., Franciskovich, J., Shultz, M., Schweitzer, B., Bishop, P., Wilson, M., and Chmielewski, J. (1997). Targeting the dimerisation interface of HIV-1 protease: Inhibition with cross-linked interfacial peptides. Journal of the American Chemical Society 119, 4841–4845.

What is claimed is:

1. A peptide comprising
   (a) said peptide comprises a β-strand-forming section, said section consisting of four to sixteen consecutive α-D-amino residues and encompassing at least 50% of the length of said peptide;
   (b) each of the consecutive α-D-amino acid residues in said β-strand-forming section has a side chain;
   (c) said β-strand-forming section forms a β-strand having a peptide backbone which takes on the form of an extended ribbon having two edges, a first edge which associates with a target β-strand formed by a separate peptide-containing molecule and a second edge, such that the NH and CO components of successive α-D-amino acid residues lie along the first edge and the second edge of the ribbon, the first edge and second edge corresponding to two opposite edges of the plane of the ribbon, and the side chains of the consecutive α-D-amino acid residues being alternatively above or below the plane of the ribbon;

(d) at least one of the Nα-atoms within the peptide backbone of the β-strand is a Nα-substituted with an Nα-substituent, such that one or more Nα-substituent lie along only the second edge and sterically hinders the association of the second edge with another β-strand; and (e) the first edge remains free of Nα-substituents, and is not prevented from associating with the target β-strand formed by the separate peptide-containing molecule.

2. The peptide according to claim 1, wherein, when there are two or more successive Nα-substituted α-D-amino acid residues, no two successive Nα-substituted α-D-amino acid residues in the β-strand-forming section are separated by more than 3 consecutive Nα-unsubstituted α-D-amino acid residues.

3. The peptide according to claim 1 wherein, when there are two or more successive Nα-substituted α-D-amino acid residues, the successive Nα-substituted α-D-amino acid residues in the β-strand-forming section are separated from each other by single Nα-unsubstituted α-D-amino acid residues, such that the β-strand-forming section comprises an alternating sequence of Nα-substituted and Nα-unsubstituted α-D-amino acid residues.

4. The peptide according to claim 1 wherein the Nα-substituent of each Nα-substituted α-D-amino acid residue in the β-strand-forming section sterically allows or promotes the β-strand-forming section to form a β-strand, and sterically hinders the association of said second edge of that β-strand with any other β-strand.

5. The peptide according to claim 4, wherein the Nα-substituent of each Nα-substituted α-D-amino acid residue in the β-strand-forming section is selected from the group consisting of:
 a fluorine atom or an OH group;
 a group that is connected to the Nα atom by an oxygen atom within it;
 a group that is connected to the Nα atom by a $CH_2$ subgroup within it;
 a methyl or ethyl group, or some other alkyl or aliphatic group;
 a substituted or unsubstituted benzyl group, or some other arylmethyl group;
 an acetylated or acylated 2-hydroxy-4-methoxybenzyl (AcHmb) group; and
 an acylated or unacylated 2-hydroxybenzyl (AcHb/Hb) group.

6. The peptide according to claim 1, wherein the side chain of each α-D-amino acid residue in the β-strand-forming section allows or promotes the α-strand forming section to form a β-strand.

7. The peptide according to claim 6, wherein the side chain of one or more α-D-amino acid residues in the β-strand-forming section is that of an amino acid residue having a β-sheet propensity of greater than 1.00.

8. The peptide according to claim 6, wherein the side chain of any one or more α-D-amino acid residues in the β-strand-forming section is selected from the group consisting of:
 an atom or group that allows or promotes the β-strand-forming section to associate as a β-strand with the target β-strand and thereby form a stable β-sheet complex; and
 an atom or group that forms a hydrophobic or electrostatic interaction, hydrogen bond, or other favourable non-covalent interaction with the neighbouring side chain of the target β-strand in a β-sheet complex comprising the target β-strand and the β-strand-forming section.

9. The peptide according to claim 6, wherein the side chain of any one or more α-D-amino acid residues in the β-strand-forming section is selected from the group consisting of:
 a hydrophobic group, or a group that has a considerable hydrophobic portion;
 a branched or unbranched alkyl or aliphatic group;
 a group that is branched at its connecting β-carbon atom;
 an aromatic group;
 an acidic or basic group; and
 an amide- or hydroxyl-containing group.

10. The peptide according to claim 1, wherein the side chain of one or more α-D-amino acid residues in the β-strand-forming section hinders stacking of β-sheets.

11. The peptide according to claim 10, wherein the side chain of one or more α-D-amino acid residues in the β-strand-forming section extends beyond the neighbouring side chains in the β-strand.

12. The peptide according to claim 1, wherein the side chain of one or more α-D-amino acid residues in the p-strand-forming section contains a detectable group which allows the peptide to be traced or detected.

13. The peptide according to claim 12, wherein the side chain of one or more α-D-amino acid residues in the β-strand-forming section is selected from the group consisting of:
 an atom or group that contains a radioactive or magnetically active nucleus;
 that of phenylalanine or tyrosine with one or more radioactive or magnetically active iodine or other halogen atoms substituted onto the aromatic ring;
 a fluorescent, coloured, or other spectroscopically detectable group;
 a group which contains an unpaired electron and thereby acts as a spin label;
 a group which contains the 2,2,5,5-tetramethyl-1-pyrrolidinyloxy (PROXYL) group; and
 a group which contains the 2,2,6,6-tetramethyl-1-piperidinyloxy (TEMPO) group.

14. The peptide according to claim 1, wherein the side chain of one or more α-D-amino acid residues in the β-strand-forming section is selected from the group consisting of the side chain of:
 any naturally occurring α-L-amino acid or synthetic derivative thereof; alanine; serine; cysteine; threonine; valine; leucine; isoleucine; methionine; phenylalanine; tyrosine; tryptophan; glutamine; asparagine; glutamate; aspartate; histidine; lysine; arginine; and
 tert-leucine or β-hydroxyvaline.

15. The peptide according to claim 1 wherein the target p-strand is formed by the Alzheimer's Aβ peptide, and the β-strand-forming section binds specifically as a β-strand to part or all of the KLVFFAE sequence (SEQ ID NO: 51) within the target α-strand in the parallel orientation, thereby forming a parallel β-sheet complex wherein consecutive residues of the β-strand-forming section lie directly opposite consecutive residues of SEQ ID NO:5 in the same order.

16. The peptide according to claim 1 wherein the target β-strand is formed by the Alzheimer's Aβ peptide, and the β-strand-forming section binds specifically as a β-strand to part or all of the KLVFFAE sequence (SEQ ID NO: 5) within the target β-strand in the antiparallel orientation, thereby forming an antiparallel β-sheet complex wherein consecutive residues of the β-strand-forming section lie directly opposite consecutive residues of SEQ ID NO:5 in reverse order.

17. The peptide according to claim 1 wherein the β-strand-forming section is preceded by, or followed by, or otherwise attached to a distinct membrane-penetrating section of the peptide which enables the β-strand-forming section to cross cell membranes, the blood-brain barrier or any other biological barrier.

18. The peptide according to claim 17 wherein the side chain of each residue in the membrane-penetrating section is selected from the group consisting of:
a basic or hydrophobic group; and a side chain of alanine, valine, leucine, isoleucine, methionine, phenylalanine, tyrosine, tryptophan, proline, histidine, lysine, or arginine.

19. The peptide according to claim 1 wherein the β-strand-forming section has a free or acylated N terminus and a free, or amidated, or esterified C terminus, or forms part of a larger peptide which has a free or acylated N terminus and a free, amidated, or esterified C terminus.

20. The peptide according to claim 1 wherein the β-strand-forming section is attached to another functional component.

21. The peptide according to claim 20, wherein the functional component is selected from the group consisting of:
a component which strengthens the binding of the β-strand-forming section to the target β-strand;
a component which enhances specificity of association of the β-strand-forming section with the target β-strand;
a component which enables the β-strand-forming section to cross cell membranes, the blood-brain barrier and other biological barrier;
a component which causes the peptide to target specific organs, cells, or molecules;
a component which allows the peptide to be traced or detected;
an atom or group that contains a radioactive or magnetically active nucleus;
a fluorescent, coloured, or other spectroscopically detectable group;
a group which contains an unpaired electron and thereby acts as a spin label;
a group which contains the 2, 2, 5, 5-tetramethyl-1-pyrrolidinyloxy (PROXYL) group or the 2, 2, 6, 6-tetramethyl-1-piperidinyloxy (TEMPO) group;
a solid matrix, resin, or support;
an enzyme, hormone, antibody, transcription factor, or other protein molecule;
a group that binds specifically to a particular protein; and
a cytotoxic molecule.

22. The peptide according to claim 20, wherein attachment of the β-strand-forming section to the functional component is by means of: an amide or ester linkage formed with the C-terminus of the β-strand-forming section; or an amide linkage formed with the N-terminus of the β-strand-forming section; or an amide linkage formed with a carboxyl, or amino group of a side chain within the β-strand-forming section; or an ester linkage formed with a carboxyl or hydroxyl group of a side chain within the β-strand-forming section; or a disulphide bridge formed with a thiol group of a side chain within the β-strand-forming section.

23. The peptide according to claim 1 wherein the β-strand-forming section comprises between 5 and 10 amino acid residues and/or includes side chains of amino acid residues of the β-strand-forming section that are homologous to or identical to the amino-acid sequence FFVLK of SEQ ID NO: 3.

24. The peptide according to claim 1 wherein the β-strand-forming section associates with a target β-strand comprising the amino-acid sequence KLVFF of SEQ ID NO: 1.

25. The peptide according to claim 1 comprising one or more components which mimic the structure and action of said β-strand-forming section, wherein the components which mimic the structure and action of the β-strand-forming section are formed by replacing one or more of the backbone peptide groups or side-chain groups of amino acid residues of the β-strand-forming section by another chemical group of similar stereochemistry and ability to form favourable non-covalent interactions with the target β-strand.

26. The peptide according to claim 25 wherein:
(a) one or more of the Nα-unsubstituted backbone peptide groups (CONH) of the β-strand-forming section is/are each replaced by any of the following groups: CSNH (thioamide); COO (ester); CSO or COS (thioester); CSS (dithioester); COCH$_2$ (ketone); CSCH$_2$ (thioketone); SO$_2$NH (sulphonamide); SOCH$_2$ (sulphoxide); SO$_2$CH$_2$ (sulphone); SO$_2$O (sulphonate); and/or
(b) one or more Nα-substituted backbone peptide groups (CON(R)) of the β-strand-forming section is/are replaced by one of the following N- or C-substituted groups: CSN(R) (thioamide); COCH(R) (ketone); CSCH(R) (thioketone); SO$_2$N(R) (sulphonamide); SOCH(R) (sulphoxide); SO$_2$C(R) (sulphone), wherein R is equivalent to the original Nα-substituent; and/or
(c) one or more of the side chains of the β-strand-forming section is/are each replaced by another group having stereochemistry or arrangement of polar and non-polar atoms, similar to that of the replaced side chains, maintaining those particular features which are essential for association with the target β-strand.

27. The peptide ording to claim 1, wherein any two successive Nα-substituted α-D-amino acid residues are separated by an odd number of consecutive Nα-ubstituted α-D-amino acid residues.

28. A pharmaceutical composition comprising the peptide according to claim 1.

\* \* \* \* \*

SEQUENCE LISTING

```
<160> NUMBER OF SEQ ID NOS: 5

<210> SEQ ID NO 1
<211> LENGTH: 5
<212> TYPE: PRT
<213> ORGANISM: Artificial Sequence
<220> FEATURE:
<223> OTHER INFORMATION: RESIDUES 16 to 20 OF HUMAN A-BETA PEPTIDE

<400> SEQUENCE: 1

Lys Leu Val Phe Phe
  1               5
```

```
<210> SEQ ID NO 2
<211> LENGTH: 6
<212> TYPE: PRT
<213> ORGANISM: Artificial Sequence
<220> FEATURE:
<223> OTHER INFORMATION: ARTIFICIAL PEPTIDE ASSOCIATES TIGHTLY WITH
      SEQUENCE OF SEQ ID NO: 1
<220> FEATURE:
<221> NAME/KEY: MOD_RES
<222> LOCATION: 2
<223> OTHER INFORMATION: METHYLATION
<220> FEATURE:
<221> NAME/KEY: MOD_RES
<222> LOCATION: 4
<223> OTHER INFORMATION: METHYLATION
<220> FEATURE:
<223> OTHER INFORMATION: all amino acid residues are the D-enantiomer

<400> SEQUENCE: 2

Leu Leu Leu Leu Arg Arg
 1               5

<210> SEQ ID NO 3
<211> LENGTH: 5
<212> TYPE: PRT
<213> ORGANISM: Artificial Sequence
<220> FEATURE:
<223> OTHER INFORMATION: REVERSE OF PEPTIDE SEQUENCE OF SEQ ID NO: 1

<400> SEQUENCE: 3

Phe Phe Val Leu Lys
 1               5

<210> SEQ ID NO 4
<211> LENGTH: 7
<212> TYPE: PRT
<213> ORGANISM: Artificial Sequence
<220> FEATURE:
<223> OTHER INFORMATION: A HOMOLOGOUS SEQUENCE OF PEPTIDE SEQUENCE OF
      SEQ ID NO: 1

<400> SEQUENCE: 4

Lys Lys Leu Val Phe Phe Ala
 1               5

<210> SEQ ID NO 5
<211> LENGTH: 7
<212> TYPE: PRT
<213> ORGANISM: Artificial Sequence
<220> FEATURE:
<223> OTHER INFORMATION: PARTIAL PEPTIDE SEQUENCE OF OF HUMAN A-BETA
      PEPTIDE

<400> SEQUENCE: 5

Lys Leu Val Phe Phe Ala Glu
 1               5
```